United States Patent
Scheibel et al.

(10) Patent No.: US 10,800,975 B2
(45) Date of Patent: *Oct. 13, 2020

(54) PROCESS FOR MAKING RENEWABLE SURFACTANT INTERMEDIATES AND SURFACTANTS FROM FATS AND OILS AND PRODUCTS THEREOF

(71) Applicant: The Procter & Gamble Company, Cincinnati, OH (US)

(72) Inventors: Jeffrey John Scheibel, Glendale, OH (US); Scott Leroy Cron, Liberty Township, OH (US); Stephen Anthony Derose, Reading, OH (US); Ryan Michael West, West Chester, OH (US); Phillip Kyle Vinson, Fairfield, OH (US); Thomas Earl Williams, Sunman, IN (US); Kevin Lee Garber, Loveland, OH (US); Praveen Kumar Depa, Hyde Park, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/972,530

(22) Filed: May 7, 2018

(65) Prior Publication Data

US 2018/0251411 A1  Sep. 6, 2018

Related U.S. Application Data

(63) Continuation of application No. 14/629,526, filed on Feb. 24, 2015, now Pat. No. 9,994,497.

(Continued)

(51) Int. Cl.
 *C10G 3/00* (2006.01)
 *C07C 2/64* (2006.01)
 (Continued)

(52) U.S. Cl.
 CPC .............. *C10G 3/50* (2013.01); *C07C 2/64* (2013.01); *C07C 5/327* (2013.01); *C07C 5/333* (2013.01);
 (Continued)

(58) Field of Classification Search
 None
 See application file for complete search history.

(56) References Cited

U.S. PATENT DOCUMENTS 7,282,474 B2 * 10/2007 Dirkzwager .......... C07C 1/0485
                                                      510/357
7,728,178 B2 *  6/2010 Greager ................... C07C 2/66
                                                      568/451

(Continued)

OTHER PUBLICATIONS

Search_report_application_No. PCT/US2015/017248, dated May 27, 2015, 10 pages.

(Continued)

*Primary Examiner* — In Suk C Bullock
*Assistant Examiner* — Alyssa L Cepluch
(74) *Attorney, Agent, or Firm* — Melissa G. Krasovec

(57) ABSTRACT

The present invention relates generally to methods for producing renewable detergent compounds. More specifically, the invention relates to methods for producing detergent intermediates, including bio-linear alkylbenzene (LAB), bio-alcohols, and long chain bio-paraffins, from natural oils.

8 Claims, 10 Drawing Sheets

Related U.S. Application Data

(60) Provisional application No. 61/944,058, filed on Feb. 25, 2014.

(51) Int. Cl.
| | | |
|---|---|---|
| *C07C 5/333* | (2006.01) | |
| *C07C 5/327* | (2006.01) | |
| *C11D 3/34* | (2006.01) | |
| *C07C 303/14* | (2006.01) | |
| *C07C 303/24* | (2006.01) | |
| *C10G 29/20* | (2006.01) | |
| *C10G 35/00* | (2006.01) | |
| *C07C 29/16* | (2006.01) | |
| *C11D 1/14* | (2006.01) | |
| *C11D 1/22* | (2006.01) | |
| *C11D 1/37* | (2006.01) | |
| *C07C 309/62* | (2006.01) | |

(52) U.S. Cl.
CPC ............ *C07C 29/16* (2013.01); *C07C 303/14* (2013.01); *C07C 303/24* (2013.01); *C07C 309/62* (2013.01); *C10G 3/00* (2013.01); *C10G 3/42* (2013.01); *C10G 29/205* (2013.01); *C10G 35/00* (2013.01); *C11D 1/146* (2013.01); *C11D 1/22* (2013.01); *C11D 1/37* (2013.01); *C11D 3/34* (2013.01); *C10G 2300/1011* (2013.01); *C10G 2300/1014* (2013.01); *C10G 2300/1051* (2013.01); *C10G 2400/30* (2013.01); *Y02P 30/20* (2015.11)

(56) References Cited

U.S. PATENT DOCUMENTS

| | | | |
|---|---|---|---|
| 7,737,312 B2 | 6/2010 | Greager | |
| 8,119,847 B2 | 2/2012 | Dindi et al. | |
| 8,338,358 B2* | 12/2012 | Bernhardt | C07C 303/06 510/495 |
| 8,502,005 B1* | 8/2013 | Bozzano | C07C 1/22 585/240 |
| 8,592,638 B2 | 11/2013 | Aalto et al. | |
| 9,005,429 B2 | 4/2015 | Markkanen et al. | |
| 9,994,497 B2 | 6/2018 | Scheibel | |
| 2004/0030200 A1* | 2/2004 | Zeller | C07C 29/16 568/876 |
| 2012/0157728 A1 | 6/2012 | Vermeiren et al. | |
| 2012/0213726 A1* | 8/2012 | Green | C07C 6/04 424/70.24 |
| 2012/0214724 A1 | 8/2012 | Scheibel et al. | |
| 2012/0266838 A1 | 10/2012 | Gosselink | |
| 2013/0253240 A1 | 9/2013 | Bozzano et al. | |
| 2013/0253243 A1* | 9/2013 | Bozzano | C10G 3/42 585/324 |
| 2013/0281751 A1 | 10/2013 | Bozzano et al. | |
| 2013/0281752 A1 | 10/2013 | Bozzano et al. | |
| 2013/0338410 A1 | 12/2013 | Wang et al. | |
| 2014/0031546 A1 | 1/2014 | Shen | |
| 2014/0255330 A1 | 9/2014 | Cron et al. | |
| 2014/0271519 A1 | 9/2014 | Schiebel et al. | |
| 2014/0364355 A1 | 12/2014 | Frey et al. | |
| 2015/0239798 A1 | 8/2015 | Scheibel et al. | |
| 2015/0240187 A1 | 8/2015 | Scheibel et al. | |

OTHER PUBLICATIONS

Search_report_application_No. PCT/US2015/017287, dated May 27, 2018, 4 pages.

* cited by examiner

PROCESS FOR MAKING RENEWABLE SURFACTANT INTERMEDIATES AND SURFACTANTS FROM FATS AND OILS AND PRODUCTS THEREOF

FIELD OF THE INVENTION

The present invention relates generally to methods for producing renewable detergent compounds. More specifically, the invention relates to methods for producing detergent intermediates, including bio-linear alkylbenzene (LAB), bio-alcohols, and long chain bio-paraffins, from natural oils.

BACKGROUND OF THE INVENTION

While detergents made utilizing surfactant intermediates, such as alkyl benzenes, 2-alkyl alcohols (e.g., Isalchem®, Sasol), and primarily linear alcohols (Neodol®, Shell), exist today, these surfactant intermediates are all made from conventional feedstocks, such as petroleum-derived ethylene, kerosene, or other petrol materials. Due to the growing environmental concerns over fossil fuel extraction and economic concerns over exhausting fossil fuel deposits, there is a demand for using an alternate feedstock for producing surfactants for use in detergents.

The most significant challenge associated with providing renewable surfactants, other than the conventional methyl ester sulphonates produced today from natural oils, is the capital cost of building entirely new production facilities. Furthermore, there is a need to provide an efficient way to produce high purity bio-paraffins for use in producing large volume, renewable detergent intermediates (e.g., detergent alcohols, linear alkyl benzene (LAB)), either as a stand-alone detergent intermediate production facility or integrated with an existing detergent intermediate production facility. Production approaches that provide both renewable detergent alcohols and renewable LAB are especially desirable. Additionally, providing long chain renewable feedstocks for the production of long chain renewable paraffin sulfonates, simultaneously with the production of renewable detergent alcohols and renewable LAB, may make the production of renewable paraffin sulfonates efficient and viable, as well.

Methods for processing natural fats, oils, and fatty acids into renewable paraffins are known. However, these known methods are largely focused on biofuels, e.g., long chain renewable diesel. Much less is known about methods for producing renewable paraffins for use in making detergent intermediates, where purity is more stringent. High purity paraffins are important for detergent intermediate manufacturing, e.g., LAB production or production of detergent alcohols, where subsequent process steps are performed (e.g., dehydrogenation, alkylation, hydroformylation), involving various catalysts. In contrast, biofuels do not require subsequent processing—biofuels are typically burned in a combustion engine. And, many of the desirable characteristics of biofuels are less desirable for detergent intermediates and detergent surfactants that are used in cleaning products. For example, the presence of impurities, such as branched compounds, unsaturated compounds, aromatic compounds, cyclic compounds, and compounds with some degree of oxygen content is often desirable in a biofuel. For detergent intermediates, however, such impurities can form undesirable products, such as quaternary structures (which may have reduced biodegradability), under standard catalytic processes. And, many of the catalysts used in the chemical processing of detergent intermediates do not tolerate impurities, such as oxygenates, residual fatty acids, esters, and substantial branching.

A process for producing linear alkylbenzenes, paraffins, and olefins from a feed source that includes a blend of natural oils, i.e., oils that are not extracted from the earth, and kerosene is known. However, the known process has limitations, namely it only allows for the supplementing of a kerosene feed with natural oils, e.g., about 12% of the feed source is natural oils.

There is, therefore, a need to produce high purity linear paraffins from renewable materials. There is also a need to provide low-cost, integrated processes that make use of existing petrol-based production facilities. In particular, there is a need to produce linear alkylbenzenes, paraffins, and olefins from a feed source that includes a blend of natural oils and kerosene (petrol-based), where the feed source contains a greater concentration of natural oil (e.g., greater than about 12% or greater than about 50% or greater than about 75%). There is also a need to provide new stand-alone production facilities (outside of existing petrol-based production facilities) to produce renewable surfactants. Renewable surfactants may be used to make sustainable detergent formulations for consumer products, to meet the needs of consumers who desire sustainable products with good performance at an affordable cost.

It has been found that by selecting certain process conditions, high purity, renewable linear paraffins may be produced from natural oils, for use in making renewable detergent intermediates, such as LAB and detergent alcohols. The process(es) of the invention may be integrated into existing petrol-based production facilities or used in stand-alone production facilities.

SUMMARY OF THE INVENTION

The present invention attempts to solve one more of the needs by providing a method for producing an alkylbenzene and a detergent alcohol from a natural oil comprising:
  a) providing a first feed stream comprising natural oil;
  b) deoxygenating the first feed stream to form a stream comprising paraffins;
  c) removing volatile components and gases from the stream comprising paraffins to form a purified paraffin stream;
  d) fractionating the purified paraffin stream into three fractions, where a first fraction comprises a lower boiling range, a second fraction comprises a middle boiling range, and a third fraction comprises a high boiling range;
  e) dehydrogenating the first fraction to form a stream comprising olefins;
  f) alkylating the stream comprising olefins with a second feed stream comprising benzene to form a stream comprising alkylbenzenes;
  g) dehydrogenating the second fraction to form a stream comprising olefins and paraffins;
  h) separating the olefins from the paraffins in the stream comprising olefins and paraffins to form an olefin stream;
  i) hydroformylating the olefin stream to form a stream comprising detergent alcohols.

The present invention further relates to detergent compositions comprising sulfonated linear alkylbenzene and/or sulfated detergent alcohol, produced according to the methods described herein.

DETAILED DESCRIPTION OF THE INVENTION

Figure 1:
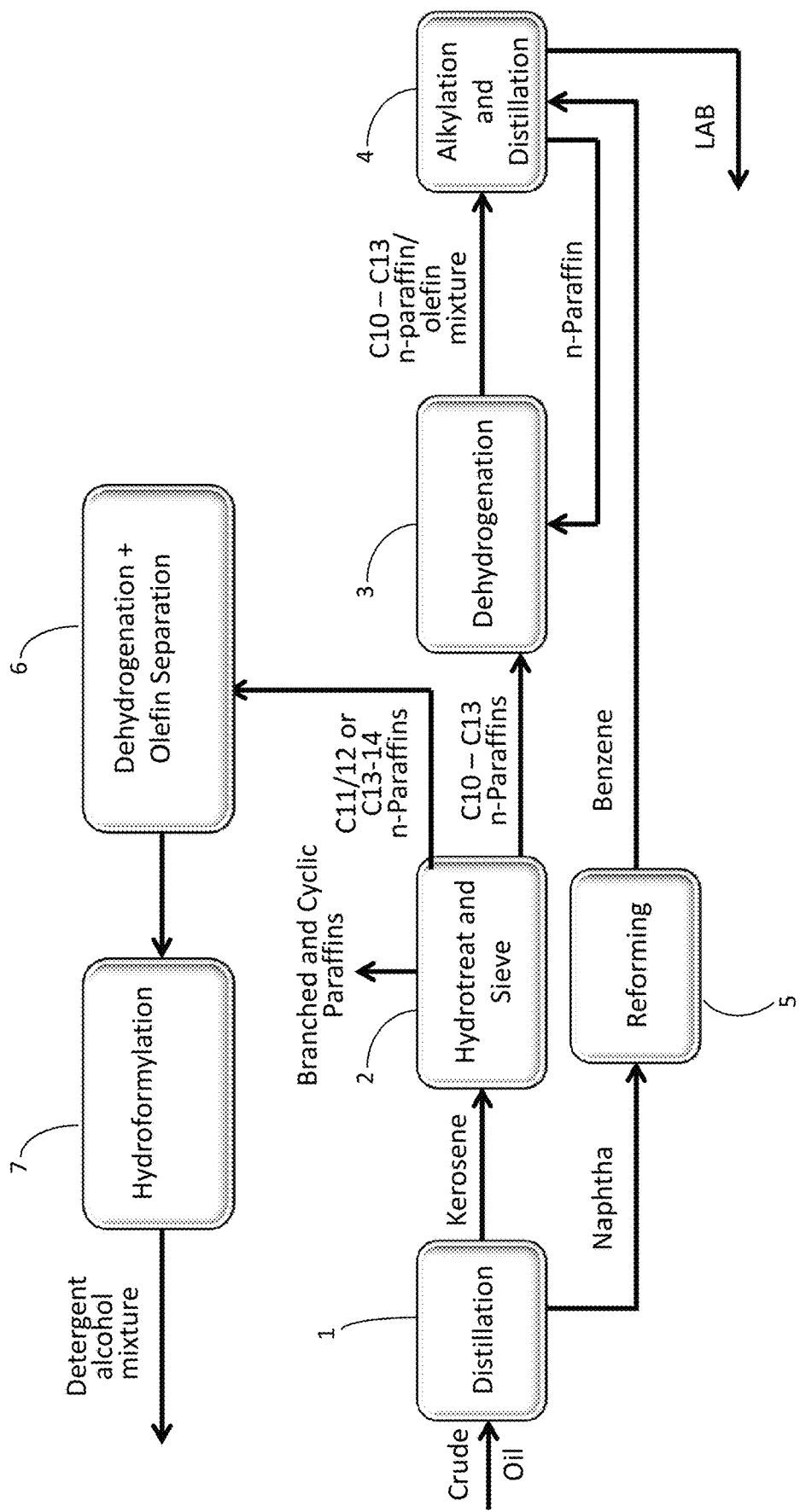
FIG. 1 schematically illustrates a commercial kerosene process for producing alkylbenzenes and detergent alcohols FIG. 2 schematically illustrates an integrated system for the production of a blend of kerosene-based and renewable alkylbenzene as well as a renewable detergent alcohol.

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, articles such as "a" and "an" when used in a claim, are understood to mean one or more of what is claimed or described.

As used herein, the terms "include", "includes" and "including" are meant to be non-limiting.

As used herein, the term "LHSV" means Liquid Hourly Space Velocity.

As used herein, the term "GHSV" means Gasous Hourly Space Velocity.

As used herein, the term "LAS" refers to linear alkylbenzene sulfonate.

As used herein, the term "LAB" refers to linear alkylbenzene.

As used herein, the term "fatty alcohol" refers to a linear alcohol derived from a natural, renewable oil via reduction of the oil to alcohol (specifically, transesterification of triglycerides to give methyl esters which in turn are hydrogenated to the alcohols). Fatty alcohols are essentially 100% linear.

As used herein, the term "detergent alcohol" is broader than the term fatty alcohol and encompasses fatty alcohols, which are essentially 100% linear, as well as synthetic alcohols, which may contain varying levels of 2-alkyl branched content, depending on the process used to make the synthetic alcohols, and linear content.

As used herein, the term "paraffin sulfonate" refers to a surfactant derived from sulfoxidation of paraffins.

As used herein, the term "renewable" (as in "renewable surfactant intermediate," "renewable linear paraffin," "renewable alkyl benzene sulfonate," "renewable alcohol sulfate," and "renewable paraffin sulfonate") refers to materials (e.g., surfactant intermediates, linear paraffins, alkyl benzene sulfonates, alcohol sulfates, paraffin sulfonates) that are derived from a renewable feedstock and contain renewable carbon. A renewable feedstock is a feedstock that is derived from a renewable resource, e.g., plants, and non-geologically derived. A material may be partially renewable (less than 100% renewable carbon content), 100% renewable (100% renewable carbon content), or somewhere in between (e.g., 50% renewable carbon content). A renewable material, for example a renewable alkylbenzene, may be blended with a non-renewable, kerosene-based material, for example, a kerosene-based alkylbenzene, to yield a partially renewable material, e.g., partially renewable alkylbenzene.

As used herein, the term "geologically derived" means derived from, for example, petrochemicals, natural gas, or coal. "Geologically derived" materials are materials that are mined from the ground (e.g., sulfur, sodium); "Geologically derived" materials cannot be easily replenished or regrown (e.g., in contrast to plant- or algae-produced oils).

"Renewable carbon" may be assessed according to the "Assessment of the Biobased Content of Materials" method, which is disclosed herein.

The terms bio- and renewable (as in "bio-paraffin" and "renewable paraffin") are used interchangeably. The term "renewable" is also synonymous with the term "sustainable," "sustainably derived," or "from sustainable sources."

The terms "kerosene-based" (as in "kerosene-based alkylbenzene") and petrol-based (as in "petrol-based alkylbenzene") are used interchangeably to refer to a material (or the production thereof) that is produced from kerosene or another petrochemical that is extracted from the earth. Kerosene-based and petrol-based materials are non-renewable.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

Method for Producing Alkylbenzene and/or Detergent Alcohol from a Natural Oil

The present invention relates to improved, highly efficient processes for making renewable surfactant intermediates and renewable surfactants, which may be used in various cleaning products. More specifically, the present invention relates to methods and systems for producing a linear paraffin or olefin product from natural oils.

As used herein, the term "natural oils" means oils that are derived from plant or algae matter (also referred to as renewable oils). Natural oils are not based on kerosene or other fossil fuels. The term "oils" include fats, fatty acids, waste fats, oils, or mixtures thereof. Natural oils include, but are not limited to, coconut oil, babassu oil, castor oil, algae byproduct, beef tallow oil, borage oil, camelina oil, Canola® oil, choice white grease, coffee oil, corn oil, *Cuphea viscosissima* oil, evening primrose oil, fish oil, hemp oil, hepar oil, jatropha oil, *Lesquerella fendleri* oil, linseed oil, *Moringa oleifera* oil, mustard oil, neem oil, palm oil, perilla seed oil, poultry fat, rice bran oil, soybean oil, stillingia oil, sunflower oil, tung oil, yellow grease, cooking oil, and other vegetable, nut, or seed oils. The natural oils typically include triglycerides, free fatty acids, or a combination of triglycerides and free fatty acids, and other trace compounds.

Suitable natural oils may contain substantial levels of detergent-range chain lengths, such as C10-18 range. The natural oil may be selected from the group consisting of coconut oil, palm kernel oil, palm oil, kernel oil, rapeseed oil, canola oil, soybean oil, algae oil, cottonseed oil, Jatropha oil, babasu oil, fish oil, linseed oil, tall oil, tallow, poultry fat, camolina, *cuphea*, and mixtures thereof. The natural oil may be selected from the group consisting of coconut oil, *cuphea*, palm kernel oil, palm oil, and poultry fat. The natural oil may be selected from the group consisting of coconut oil, palm kernel oil, *cuphea*, and palm oil. These oils contain the greatest concentration of triglycerides and free fatty acids having chain lengths ranging from C10 to C18, particularly C10 to C16, which are especially useful in the detergent industry. The natural oil feed stream may comprise triglycerides and free fatty acids in the C10 to C18 chain length or in the C10 to C16 chain length.

For reference, FIG. 1 illustrates the main processing steps of an existing, conventional LAB and detergent alcohol facility that uses kerosene extracted from the earth as a feed source. Crude oil is first distilled 1 to form kerosene and naphtha. The naptha is reformed 5 to form benzene. The kerosene is hydrotreated and sieved 2 to form C10-C13 n-paraffins, C11-12 or C13-C14 n-paraffins, branched paraffins, and cyclic paraffins. The C10-C13 n-paraffins are dehydrogenated 3 to form a C10-C13 n-paraffin/olefin mixture. The C10-C13 n-paraffin/olefin mixture is alkylated 4 with benzene to form linear alkylbenzene, and the remaining n-paraffin is distilled out. The C11/12 or C13-14 n-paraffins are dehydrogenated 6 to form olefins, which are then separated out. The olefins are hydroformylated 7 to form a mixture of detergent alcohol. The detergent alcohols produced may vary, depending on the selection of the hydroformylation catalyst in the hydroformylation unit 7. Any number of detergent alcohols may be produced, including those containing some degree of 2-alkyl branching. The detergent alcohols may contain substantial amounts of linear detergent alcohols, depending on the choice of the hydroformylation catalyst. These detergent alcohols are different from the known renewable alcohols derived from methyl esters, such as CO-1214, CO-1270.

In a typical LAB and detergent alcohol co-production facility, as shown in FIG. 1, large amounts of kerosene are fed into the hydrotreatment unit 2 for processing. Consequently, large amounts of material are fed into the sieving unit 2 as well, since much of the kerosene feedstock contains large amounts of cyclic, aromatics, branched paraffins, some lower levels of sulfur containing compounds, oxygenates, olefins, and, sometimes, nitrogen-containing compounds.

Hydrotreatment (also referred to as hydroprocessing) is a class of catalytic processes in a refinery scheme that comprises a set of reactions. Hydrotreating involves non-destructive hydrogenation and is used to improve the quality of petroleum distillates without significant alteration of the boiling range. Hydrotreating generally employs mild temperature and hydrogen pressures (in particular, as compared to the conditions of the process(es) of the invention), such that only the more unstable compounds that might lead to the formation of gums, or insoluble materials, are converted to more stable compounds. Hydrotreament is used to substantially remove sulfur, oxygenates, nitrogen, and aromatics prior to the sieving operation. Kerosene hydrotreatment units, kerosene hydrotreatment catalysts, process conditions, and configurations are well known in the petroleum art. In regard to hydrotreating kerosene, kerosene contains very low levels of oxygenates, as compared to natural oils. Therefore, the process of hydrotreating kerosene, as known and described in the art, may produce very different results when applied to natural oils (as shown in the known system of FIG. 3).

A typical kerosene composition contains between about 30% and about 50% linear paraffin. Thus, the hydrotreatment and sieving units are quite large versus other processes in the plant. Furthermore, to attain high purity of the linear paraffin, e.g., greater than 99% purity, the sieving unit cannot remove all the linear paraffin cost effectively while maintaining the very high purity required. Substantial loss of linear paraffin to the reject stream—the branched, cyclic, and some linear paraffin product from sieving unit—occurs and may only be used for jet fuel. Thus, expansion of any facility utilizing more kerosene feed would require expansion of the hydrotreatment and the sieving units.

In contrast, the deoxygenation of natural oils yields a much greater linear paraffin content—some 70-85% of the oil feedstock is renewable paraffin (versus only the sieved amount obtained from a kerosene unit—some 20-30% linear high purity paraffin). Thus, integrating the processes of the invention into an existing, conventional LAB and/or a detergent alcohol production plant, which utilizes kerosene feedstocks, may add substantially to the overall productivity of the subsequent processing steps in the kerosene-derived surfactant intermediates plant (e.g., by potentially greater than twice the kerosene production alone based on the feed required to produce the same amount of surfactant intermediate).

Figure 2:
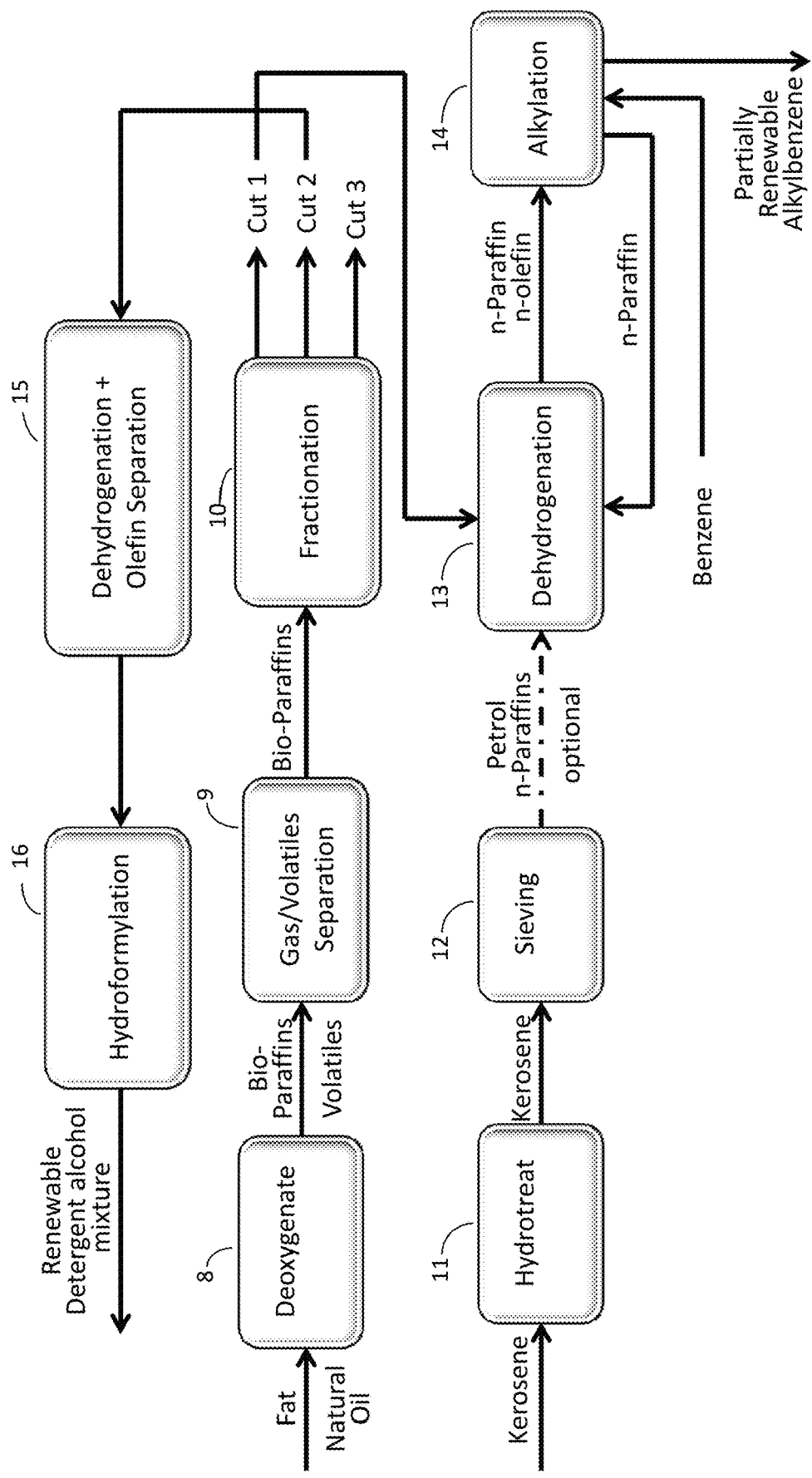
FIG. 2a schematically illustrates the production of paraffin sulfonate from one of the cuts of paraffin produced in FIG. 2.
Figure 2A:
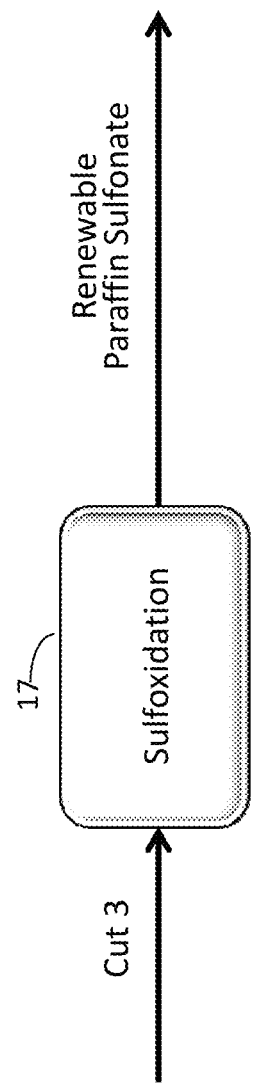

The processes of the invention may be integrated into an existing, conventional LAB or a detergent alcohol production plant (or a combined LAB and detergent alcohol production plant), which utilizes kerosene feedstocks, thereby providing renewable linear paraffin intermediates that can be integrated into the plant to provide a source of renewable carbon. Such an integrated process allows for the minimization of additional capital expense, provides a high purity renewable linear paraffin intermediates for integration into the plant, and may efficiently increase the total production output of a facility without increasing the kerosene-based units (e.g., kerosene hydrotreatment or absorptive separation (sieving)). As illustrated in FIG. 2, the process(es) of the invention 8, 9, 10 may be readily integrated into an existing, conventional LAB and/or a detergent alcohol production plant downstream 13 from sieving unit 12, thereby maximizing the renewable content of the LAB and/or detergent alcohol (as well as, paraffin sulfonate, as shown in FIG. 2a) produced in the facility without increasing the kerosene-based units 11, 12, e.g., kero-hydrotreater.

Figure 3:
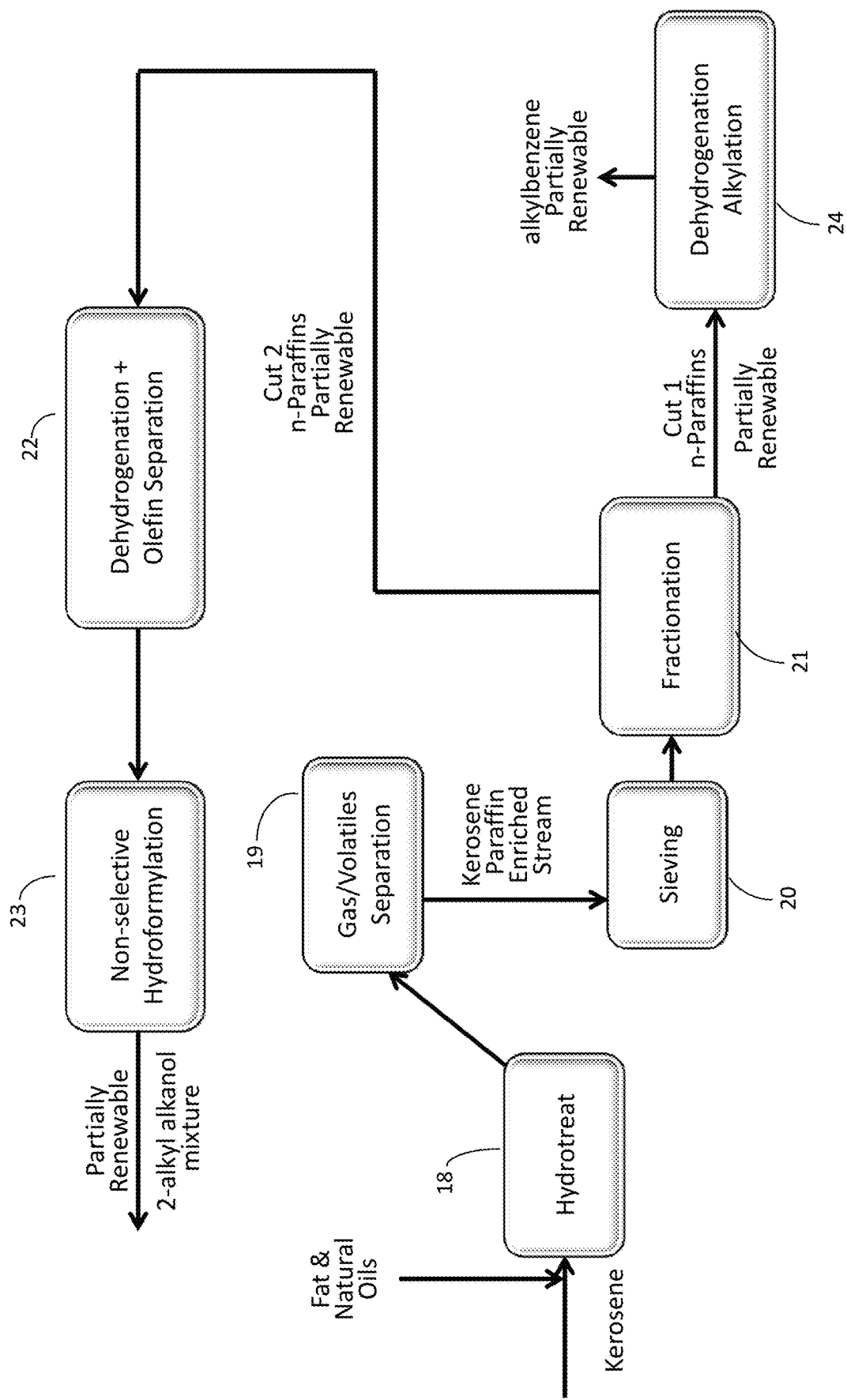
FIG. 3 schematically illustrates a known system for producing linear alkylbenzenes, paraffins, and olefins from a feed source that includes a blend of natural oils and kerosene.

In contrast, a known process for producing linear alkyl-benzenes, paraffins, and olefins from a feed source that includes a blend of natural oils, i.e., oils that are not extracted from the earth, and kerosene is shown in FIG. 3. Importantly, in this known process, the kerosene (e.g., a heart cut, C10-C13, stream of kerosene) and the natural oil are both processed in a conventional kerosene-based unit, such as a kero-hydrotreater 18. Hydrotreatment is followed by a step of removing volatile components and gases 19, sieving 20, and fractionating 21, followed by either dehydrogenation and alkylation 24 or dehydrogenation 22, olefin separation 22, and non-selective hydroformylation 23. Importantly, the kero-hydrotreater 18 receives both the kerosene stream (e.g., a heart cut, C10-C13, stream of kerosene) and the natural oil feed stream. The kero-hydrotreater 18 is employed to treat the heart cut stream of hydrocarbons to reduce the naturally occurring nitrogen and sulfur content in kerosene to acceptable levels for use in detergents. The kero-hydrotreater 18 is also configured to deoxygenate the natural oil feed to produce paraffins. The use of the kero-hydrotreater 18 to process both the kerosene and the natural oil places limitations on the process, namely it only allows for the supplementing of a kerosene feed with natural oils, e.g., about 12% of the feed source is natural oils.

As illustrated in FIG. 2, a petroleum-derived linear paraffin stream may be co-fed with a renewable linear paraffin stream, typically after a sieving step or a dehydrogenation step (FIG. 2 shows after the sieving step), to produce, for example, a partially renewable linear alkyl benzene. Depending on the volume production desired, it may also be advantageous for production efficiency to blend a petroleum-derived linear paraffin stream with a renewable paraffin stream for the production of detergent alcohols 15, 16.

As shown in FIG. 2, the processes of the invention may employ separate natural oil processing units 8, 9 that may be integrated into an existing, conventional LAB and/or detergent alcohol production plant, such that the paraffin produced by these units or fractions thereof (the paraffin may be fractionated into selected cuts in a fractionation unit 10) flows into the existing, conventional equipment downstream 13 from the sieving unit 12. This allows the renewable content of the feed source to be maximized (e.g., greater than about 12% of the feed source is natural oils, or greater than about 50% of the feed source is natural oils, or greater than about 75% of the feed source is natural oils) without increasing the kerosene-based unit(s) for hydrotreating 11, e.g., kero-hydrotreater, and sieving 12, thereby maximizing the renewable content of the LAB and/or detergent alcohol (as well as, paraffin sulfonate, as shown in FIG. 2a) produced in the facility.

More specifically, in FIG. 2, the natural oil feed stream is delivered to a deoxygenation unit 8, which also receives a hydrogen feed. In the deoxygenation unit 8, the triglycerides and fatty acids in the feed are deoxygenated and converted into linear paraffins. Structurally, triglycerides are formed from three, typically different, fatty acid molecules that are bonded together with a glycerol bridge. The glycerol molecule includes three hydroxyl groups (HO—), and each fatty acid molecule has a carboxyl group (—COOH). In triglycerides, the hydroxyl groups of the glycerol join the carboxyl groups of the fatty acids to form ester bonds. During deoxygenation, the fatty acids are freed from the triglyceride structure and are converted into linear paraffins. The glycerol is converted into propane, and the oxygen in the hydroxyl and carboxyl groups is converted into either water or carbon dioxide. The deoxygenation reactions for fatty acids and triglycerides, respectively, are illustrated below:

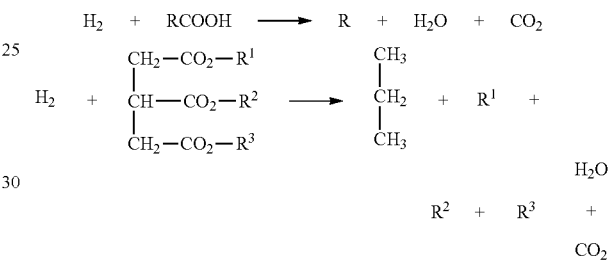

During the deoxygenation reaction, the length of a product paraffin chain $R''$ will vary by a value of one, depending on the exact reaction pathway. For example, if carbon dioxide is formed, then the chain will have one fewer carbons than the fatty acid source ($R''$). If water is formed, then the chain will match the length of the $R''$ chain in the fatty acid source. Typically, due to the reaction kinetics, water and carbon dioxide are formed in roughly equal amounts, such that equal amounts of $C_x$ paraffins and $C_{x-1}$ paraffins are formed. The deoxygenation process step, however, may be tuned (by selecting particular catalysts and conditions) to produce a C8 to C18 linear paraffin product of suitable purity (as may be measured by gas chromatography (GC) analysis of the linear paraffin product). For example, for a feedstock that is C12, the deoxygenation process may be tuned to alter the ratio of C11:C12 in the linear paraffin product, e.g., the deoxygenation process may be tuned to produce almost 100% C12 linear paraffin product.

In FIG. 2, deoxygenation 8 is followed by a step of removing volatile components and gases 9; a deoxygenated stream containing linear paraffins and volatile components and gases, such as water, carbon dioxide, and propane, exits the deoxgenation unit 8 and is fed to a separator 9. The separator 9 may be a multi-stage fractionation unit, distillation system, or a similar known apparatus. The separator 9 removes the volatile components and gases from the deoxygenated stream. After the volatile components and gases are removed, a purified renewable linear paraffin stream is formed. The purified linear bio-paraffin stream may have greater than 90% purity. The purified linear bio-paraffin stream may have a branched paraffin content of less than about 5%, an olefin and cyclic content of less than about 3%, and an alcohol, ester, aldehyde, and fatty acid content of less than about 2%.

The purified linear bio-paraffin stream may have greater than 95% purity. The purified linear bio-paraffin stream may have a branched paraffin content of less than about 3%, an olefin and cyclic content of less than about 1%, and an alcohol, ester, aldehyde and fatty acid content of less than about 1%. The purified linear bio-paraffin stream may have greater than 98% purity. The purified linear bio-paraffin stream may have a branched paraffin content of less than about 1.8%, an olefin and cyclic content of less than about 0.1%, and an alcohol, ester, aldehyde and fatty acid content of less than about 0.1%.

The process(es) described herein may be used to obtain a renewable linear paraffin having a purity of from about 90% to about 100%, or from about 93% to about 100%, or from about 95% to about 100%, or from about 98% to about 100%.

As shown in FIG. 2, the purified bio-paraffin stream may be fed into a fractionation unit 10, which separates the purified bio-paraffins into various desirable chain length fractions or cuts. For example, as shown in FIG. 2, the purified bio-paraffin stream is fractionated into three cuts or fractions. Any number of fractions may be selected, depending on how many fractions are desired. A first fraction of purified bio-paraffins may comprise lower boiling range bio-paraffins, a second fraction may comprise middle boiling range bio-paraffins, and a third fraction may comprise high boiling range bio-paraffins. The first fraction of purified bio-paraffins may comprise carbon chain lengths of C10 to C14. Suitable fractions may include various combinations of chain lengths. For example, the first cut may be C10 to C12, the second cut may be C13 to C14, and the third cut may be C15 to C18. Alternatively, the first cut may contain C10 to C13, the second cut may contain C14 to C16, and the third cut may contain C17 to C18. The cuts or fractions may be selected to maximize the efficiency of the plant, by producing individual cuts or various blends of cuts. Flexibility in terms of fractionation also allows one to address the various needs of the detergents manufacturer, including performance needs.

The first fraction of purified bio-paraffins may have carbon chains lengths having a lower limit of $C_M$, where M is an integer from four to thirty-one, and an upper limit of $C_N$, where N is an integer from five to thirty-two. The second fraction of purified bio-paraffins may have carbon chains shorter than, longer than, or a combination of shorter and longer than, the chains of the first fraction of purified bio-paraffins.

The purified bio-paraffin stream may be fractionated into three cuts. As shown in FIG. 2, the first cut of purified bio-paraffin may be fed into an alkylbenzene production unit(s) 13, 14, and the second cut may be fed into an alcohol production unit(s) 15, 16. As shown in FIG. 2a, the third cut may optionally be fed into a sulfoxidation unit 17 to form paraffin sulfonate.

More specifically, the first cut of purified bio-paraffin may be fed into a dehydrogenation unit 13 and dehydrogenated to form a stream comprising olefins and paraffins. Typically, dehydrogenation occurs through known catalytic processes, such as the commercially popular Pacol™ process. The stream comprising olefins and paraffins is then alkylated 14 with a second feed stream comprising benzene to form a stream comprising alkylbenzenes, as shown in FIG. 2. Any residual paraffin may be fed back into the dehydrogenation unit, as shown in FIG. 2. The second cut of purified bio-paraffin may be fed into a dehydrogenation unit and dehydrogenated to form a stream comprising olefins and paraffins 15. The stream comprising olefins and paraffins may then fed into an olefin absorptive separation unit to separate the olefins from the paraffins 15. In FIG. 2, the dehydrogenation step and the separation step are shown as part of a single unit 15. The olefins may then be subjected to hydroformylation 16 to form detergent alcohols. The steps of fractionation, sieving (for both linear paraffin and linear olefin), dehydrogenation, alkylation, and hydroformylation, as diagramed in the figures included herein, are well known in the art.

Thus, two renewable detergent intermediates and, optionally, a paraffin sulfonate may be produced in a single production plant. Alternatively, the first cut may be fed into an alcohol production unit to prepare shorter chain, renewable detergent alcohols. And, the third cut may be fed into a detergent alcohol unit to produce longer chain renewable detergent alcohols.

The renewable alkyl benzene and the renewable detergent alcohol may further be sulfonated and sulfated by standard means to provide renewable surfactants for use in detergent formulations.

The invention also relates to mixtures of renewable alkylbenzene sulfonate and renewable alcohol sulfate for use in detergent formulations. Mixtures of renewable alkylbenzene sulfonate, renewable alcohol sulfate, and renewable paraffin sulfonate may also be obtained. Furthermore, the renewable surfactants produced by the method(s) disclosed herein may be combined with natural alcohol sulfates or natural alcohol ethoxylated sulfates, such as those derived from the reduction of methyl esters to fatty alcohols. Such mixtures provide even greater flexibility to the detergent formulator. Such mixtures also provide improved performance for the consumer who desires a renewable formulation.

The invention also relates to a detergent composition that comprises a renewable surfactant content of at least about 50%, or at least about 70%, or at least about 80%, or at least about 90% (meaning that at least about 50%, or at least about 70%, or at least about 80%, or at least about 90% of the total surfactant in the detergent composition is renewable).

Figure 4:
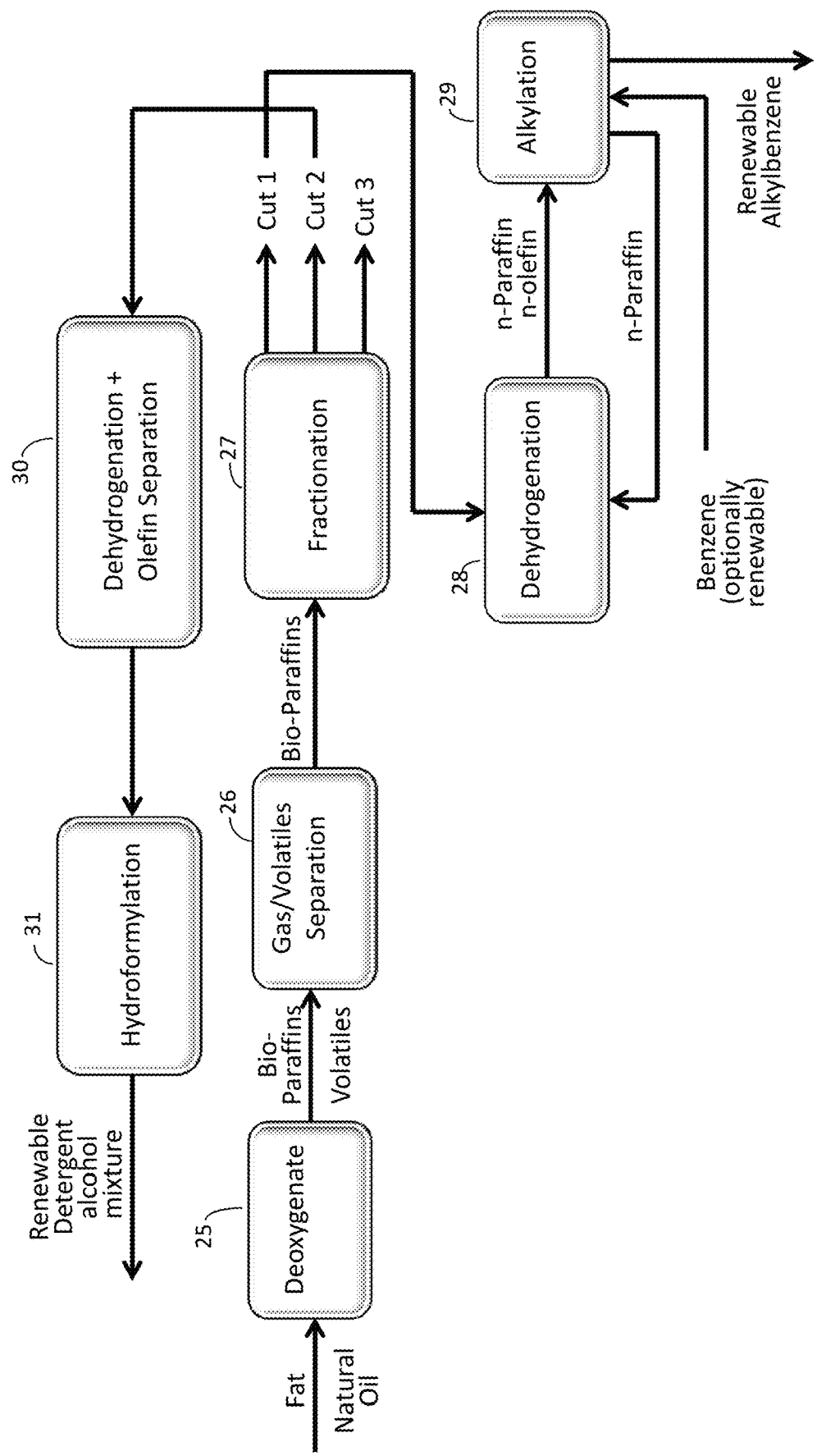
FIG. 4 schematically illustrates a stand-alone system (outside of a conventional kerosene facility) to produce renewable linear paraffins, which are subsequently processed to produce renewable detergent alcohol and renewable alkylbenzene.

The processes of the invention may also be utilized in stand-alone units to produce renewable linear paraffins, outside of a conventional kerosene facility; this may be economical for subsequent introduction into a kerosene production facility or a facility that produces LAB from purchased paraffin sources. FIG. 4 illustrates such a use. As shown in FIG. 4, the natural oil is deoxygenated 25, and deoxygenation 25 is followed by a step of removing volatile components and gases 26, to form a purified bio-paraffin. The purified bio-paraffin may be fractionated 27 into any number of cuts, e.g., three cuts. Any one of the cuts or combinations of cuts of purified bio-paraffin may be used to prepare various renewable detergent alcohols. In FIG. 4, the second cut is shown for illustration, but any combination of carbon cuts may be produced to make various detergent alcohols, e.g., by blending the various cuts or combinations of cuts into renewable detergent alcohols. In FIG. 4, the second cut is fed into an alcohol production unit(s) 30, 31 (to dehydrogenate the second cut 30, separate out olefins 30, and hydroformylate the olefins 31) and the first cut is fed into an alkylbenzene production unit(s) 28, 29 (to dehydrogenate 28 and alkylate 29 the first cut).

Also, if renewable CO is used in the hydroformylation step 31 and/or renewable benzene is used in the alkylation step 29, a 100% renewable detergent alcohol mixture and/or a 100% renewable alkylbenzene may be produced. Otherwise, a partially renewable detergent alcohol mixture and/or a partially renewable alkylbenzene may be produced.

Figure 5:
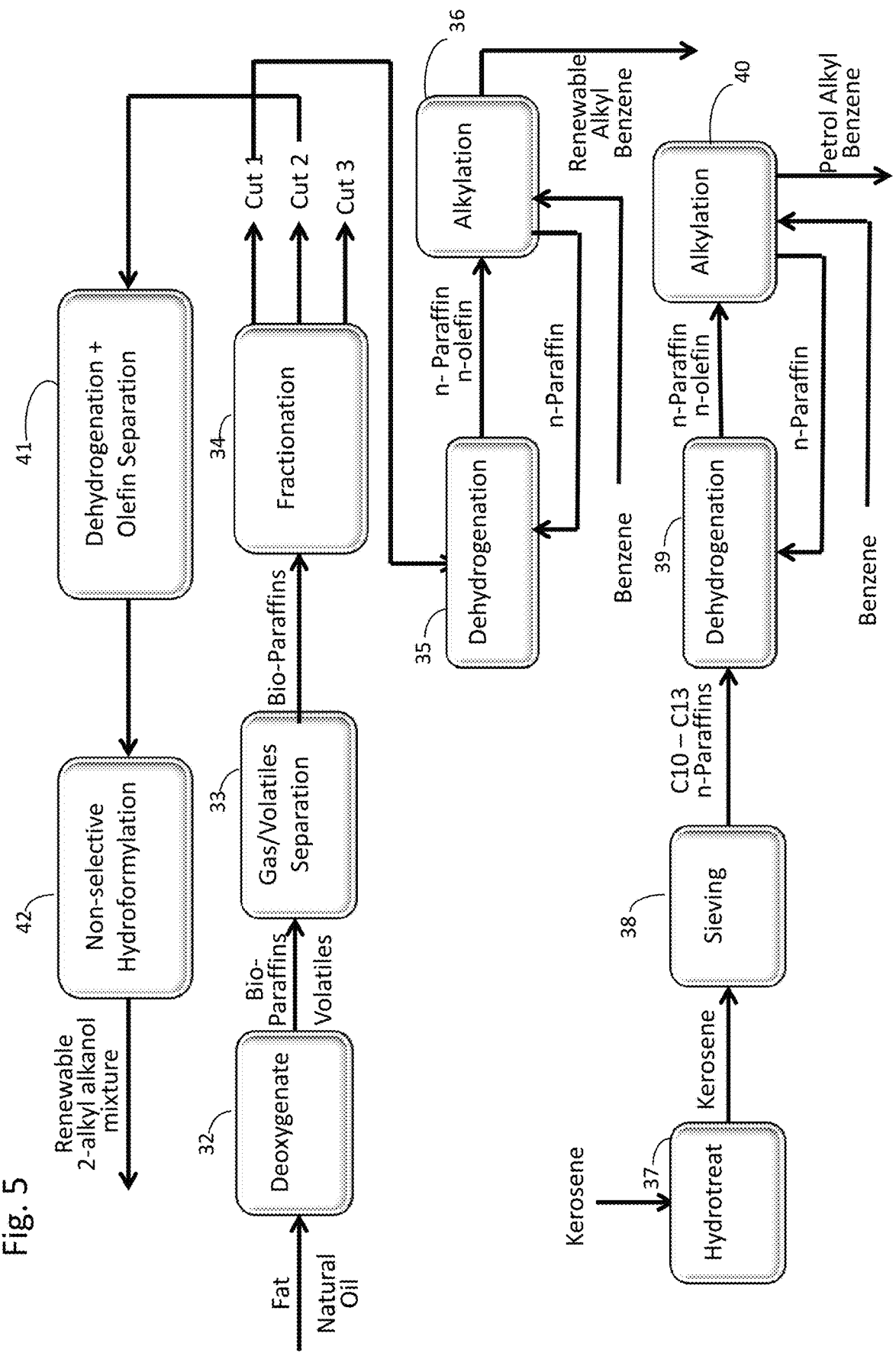
FIG. 5 schematically illustrates a system where a renewable LAB, made using the processes of the invention, is blended with a conventional, petrol-based LAB.

All in all, the processes described herein allow for maximum flexibility in terms of incorporating renewable carbon content to produce renewable surfactants. For example, FIG. 5 shows a system where a renewable LAB, made using the processes of the invention, is blended with a conventional, petrol-based LAB. As shown in FIG. 5, the natural oil is deoxygenated 32, and deoxygenation 32 is followed by a step of removing volatile components and gases 33, to form a purified bio-paraffin. The purified bio-paraffin may be fractionated 34 into any number of cuts, e.g., three cuts. In FIG. 5, the second cut is fed into an alcohol production unit(s) 41, 42 (to dehydrogenate the second cut 41, separate out olefins 41, and non-selectively hydroformylate the olefins 42). And, the first cut is fed into an alkylbenzene production unit(s) 35, 36 (to dehydrogenate 35 and alkylate 36 the first cut) to produce renewable alkyl benzene, which may be blended with a petrol-based alkyl benzene. The petrol-based alkyl benzene is produced from kerosene, which is hydrotreated 37, sieved 38, dehydrogenated 39, and alkylated 40.

Figure 6:
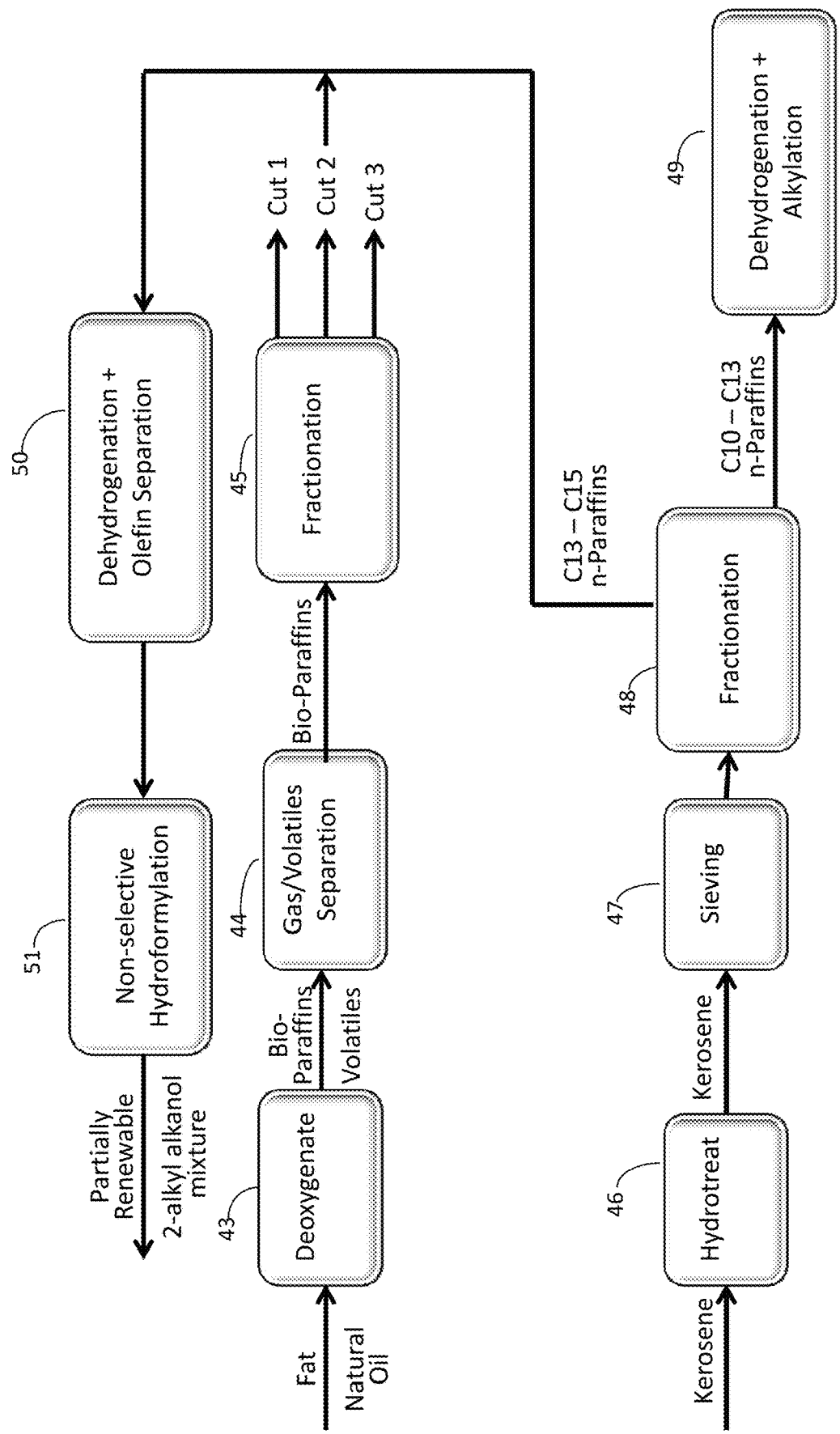
FIG. 6 schematically illustrates a system where a cut of bio-paraffin is blended with a cut of kerosene-based paraffin and subsequently processed to form a partially renewable 2-alkyl alkanol.

Also, FIG. 6, for example, shows a system where a second cut of bio-paraffin (which is made using the processes of the invention) comprising, e.g., middle boiling range bio-paraffins, is blended with a long-chain cut, e.g., C13-C15, of kerosene-based paraffin, and subsequently processed to form a partially renewable (blended) 2-alkyl alkanol. As shown in FIG. 6, the natural oil is deoxygenated 43, and deoxygenation 43 is followed by a step of removing volatile components and gases 44, to form a purified bio-paraffin. The purified bio-paraffin may be fractionated 45 into any number of cuts, e.g., three cuts. In FIG. 6, the second cut of purified bio-paraffin is blended with a petrol-based paraffin, e.g., C13-C15 paraffin, and the blend is fed into an alcohol production unit(s) 50, 51 (to dehydrogenate the blend 50, separate out olefins 50, and non-selectively hydroformylate the olefins 51). A different cut of petrol-based paraffin, e.g., C10-C13, is fed into an alkylbenzene production unit(s) 49 (to dehydrogenate and alkylate the cut) to produce petrol-based alkyl benzene. The petrol-based paraffin is produced from kerosene, which is hydrotreated 46, sieved 47, and fractionated 48.

Figure 8:
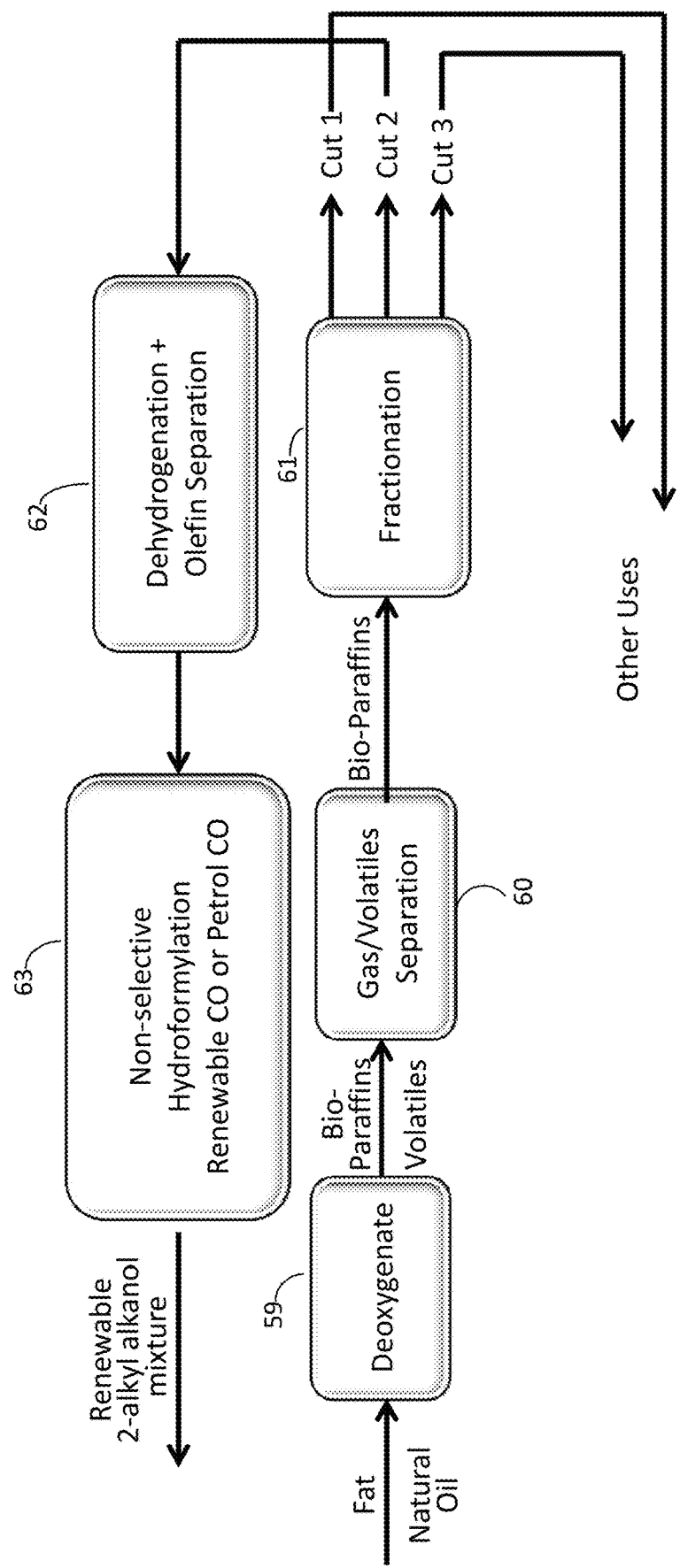

Also, FIG. 8, for example, shows a system where a renewable 2-alkyl alkanol mixture is formed. As shown in FIG. 8, the natural oil is deoxygenated 59, and deoxygenation 59 is followed by a step of removing volatile components and gases 60, to form a purified bio-paraffin. The purified bio-paraffin may be fractionated 61 into any number of cuts, e.g., three cuts. In FIG. 8, the second cut of purified bio-paraffin is fed into an alcohol production unit(s) 62, 63 (to dehydrogenate the second cut 62, separate out olefins 62, and non-selectively hydroformylate the olefins 63). The remaining cuts of purified bio-paraffin are employed for other uses.

Figure 9:
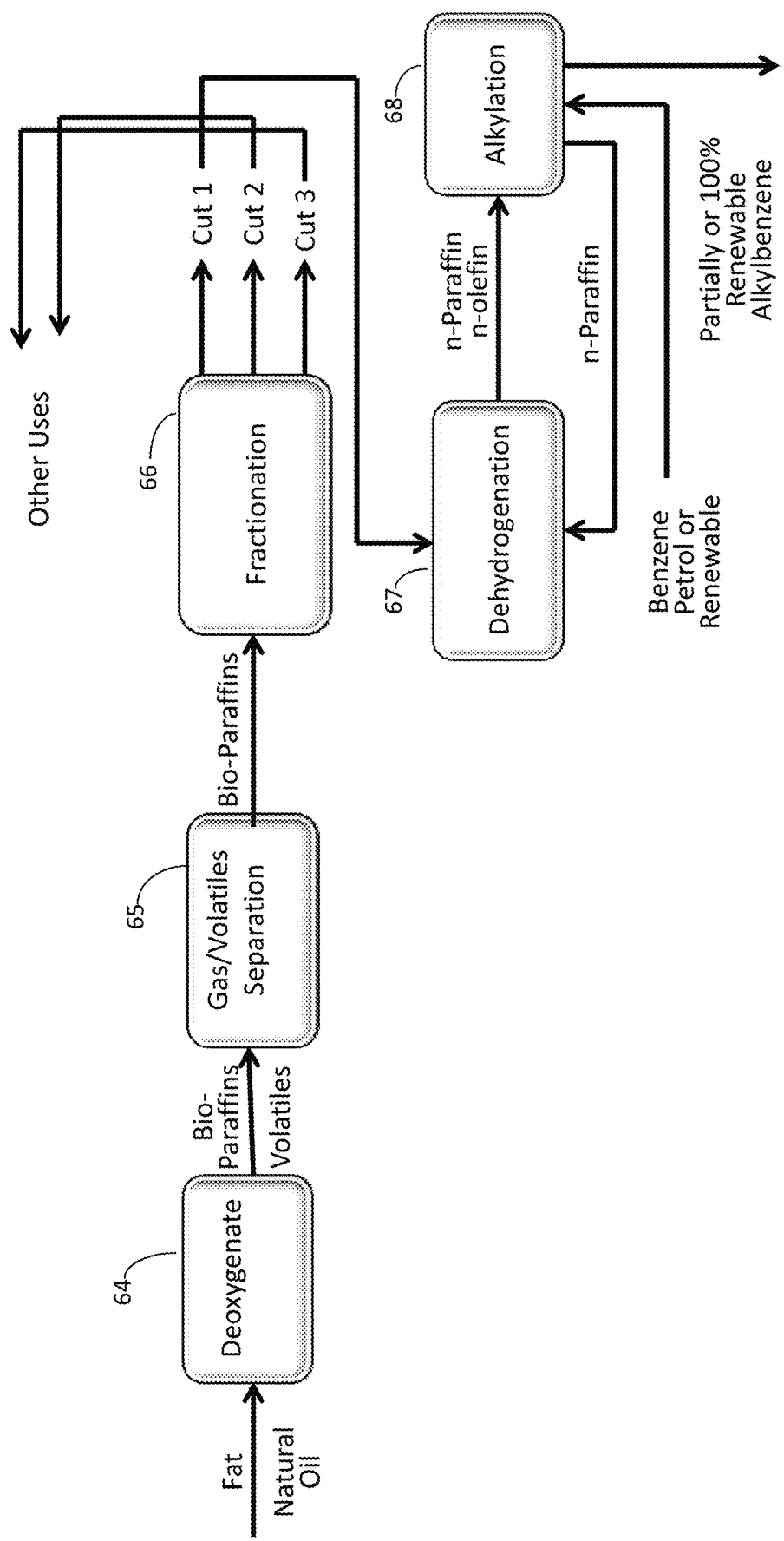
FIG. 9 schematically illustrates a stand-alone system (outside of a conventional kerosene facility) to produce renewable linear paraffins, which are subsequently processed to produce renewable alkylbenzene (with residual cuts of bio-paraffin going to other uses).

Also, FIG. 9, for example, shows a system where a renewable alkylbenzene is formed. As shown in FIG. 9, the natural oil is deoxygenated 64, and deoxygenation 64 is followed by a step of removing volatile components and gases 65, to form a purified bio-paraffin. The purified bio-paraffin may be fractionated 66 into any number of cuts, e.g., three cuts. In FIG. 9, the first cut of purified bio-paraffin is fed into an alkylbenzene production unit(s) 67, 68 (to dehydrogenate 67 and alkylate 68 the first cut) to produce a renewable alkyl benzene. The remaining cuts of purified bio-paraffin are employed for other uses.

Deoxygenation

It has been found that the deoxygenating step of the processes described herein may be an important step in order to prepare the partially or 100% renewable detergent alcohol mixture and/or the renewable alkylbenzene of the invention. In typical processing of natural oils, e.g., for biofuels, minor impurities, such as oxygenates, aromatics, cyclic and branched materials, are actually preferred for fuel mixtures. However, this is not the case in preparing surfactant intermediates for use in consumer goods, such as laundry detergents and dish products. It has been discovered that by selecting certain catalysts, process design, and reaction conditions, such as hydrogen flow rate, hydrogen pressure, temperature, and liquid flow rates, high purity bio-paraffin, suitable for detergent intermediate processing, may be produced. Certain deoxygenation conditions may be particularly advantageous for producing a high purity, renewable linear paraffin stream from natural oils.

The method of deoxygenating a natural oil stream may comprise the step(s) of reacting the natural oil stream in the presence of a Ni/Mo catalyst or a Co/Mo catalyst, at a temperature from about 340° C. to about 410° C., at a hydrogen pressure from about 500 psi to about 2000 psi, or from about 500 psi to about 1500 psi, at a GHSV from about 800 to about 2000, and at a LHSV of about 0.25 to about 6, or about 0.25 to 4.0, or about 0.5 to about 2.5.

The method of deoxygenating a natural oil stream may comprise the step(s) of reacting the natural oil stream in the presence of a Ni/Mo sulfurized catalyst or a Co/Mo sulfurized catalyst, at a temperature from about 280° C. to about 360° C., at a hydrogen pressure from about 500 psi to about 1500 psi, at a GHSV of about 800 to about 2000, and at a LHSV of about 0.25 to about 4.0, or 0.5 to about 2.5. The use of a sulferized catalyst versus a non-sulferized catalyst may affect the ratio of chain lengths in the paraffin product. Instead of using a presulfurized catalyst, the method of deoxygenating may include the use of dimethyldisulfide (DMDS) at low levels, e.g., about 0.1% to about 2% DMDS. The use of presulfurized or sulfurized catalysts may require $SO_2$ removal after deoxygenation. Suitable commercial presulfurized deoxygenation catalysts include Criterion 534® SH (PS—CoMo) and Albemarle KF-841 ® (PS—NiMo). Suitable commercial deoxygenation catalysts are also available from UOP, Johnson Matthey, IFP, Clariant, and Criterion.

The method of deoxygenating a natural oil stream may comprise the step(s) of reacting the natural oil stream in the presence of a Pd on alumina catalyst, at a temperature from about 370° C. to about 420° C., at a hydrogen pressure from about 200 psi to about 1000 psi, at a GHSV of about 800 to about 2000, and at a LHSV of about 0.25 to about 4.0, or about 0.5 to about 2.5. As discussed above, one may tune the process within the disclosed ranges of conditions to achieve an even greater purity, for example 95% purity or greater than 98% purity renewable linear paraffins. Suitable catalysts are available from Johnson Matthey or other suppliers of palladium catalysts. A suitable catalyst is 1-5% Pd on alumina or 1-5% Pd on carbon.

The deoxygenation conditions described above for the specific types of catalysts, e.g., Ni/Mo and Co/Mo catalysts, have been found to produce high purity renewable linear paraffins, e.g., a purity of greater than about 90%. Typically, if the temperature is too high, then branched paraffins are produced and cracking of the paraffin by the catalyst may also occur. If the pressure is too low, then olefins, fatty acids, and fatty alcohols may be formed; these olefins, fatty acids, and fatty alcohols are contaminants for subsequent processing steps. The selection of GHSV and LHSV rates has also been found to contribute to the production of high purity renewable linear paraffins. In general, by selecting all five conditions—the catalyst, temperature, hydrogen pressure, GHSV, and LHSV—one can produce the high purity renewable linear paraffins of the invention. Furthermore, one may tune the deoxygenation process(es) described herein within the disclosed ranges of conditions to obtain a renewable linear paraffin having an even greater purity, for example, greater than about 95% purity or greater than about 98% purity. Additional suitable commercial deoxygenation catalysts for use in the invention include Haldor Topsoe TK-527® (Ni/Mo), Albemarle KF-848 ® (Ni/Mo), Haldor Topsoe TK-574 ® (Co/Mo). Suitable commercial deoxygenation catalysts are also available from UOP, Johnson Matthey, IFP, Clariant, and Criterion.

Any of the methods of deoxygenating described herein may be used in any of the various systems described herein (e.g., FIGS. 2-10) to prepare the renewable detergent alcohols and/or renewable alkylbenzenes (and/or renewable paraffin sulfonates) of the invention. A continuous flow reactor with the ability to have counter-current hydrogen gas flow may be used for any of the methods of deoxygenating described herein.

Dehydrogenation and Hydroformylation

Any number of known catalysts may be used for dehydrogenation and hydroformylation. Furthermore, it is also know to produce high purity olefins via separation on various adsorbents, e.g., available from UOP. Any type of hydroformylation may be used to prepare the renewable detergent alcohols of the invention, such as selective or non-selective hydroformylation. Suitable selective catalysts may be obtained from Shell and suitable non-selective catalysts may be obtained from Johnson Matthey, which supplies catalysts based on rhodium or cobalt. A suitable catalyst is of the non-selective type and provides a substantial degree of 2-alkyl alkanol formation, for example, greater than 25% 2-alkyl alkanol, or greater than 50%, or greater than 90%.

Figure 7:
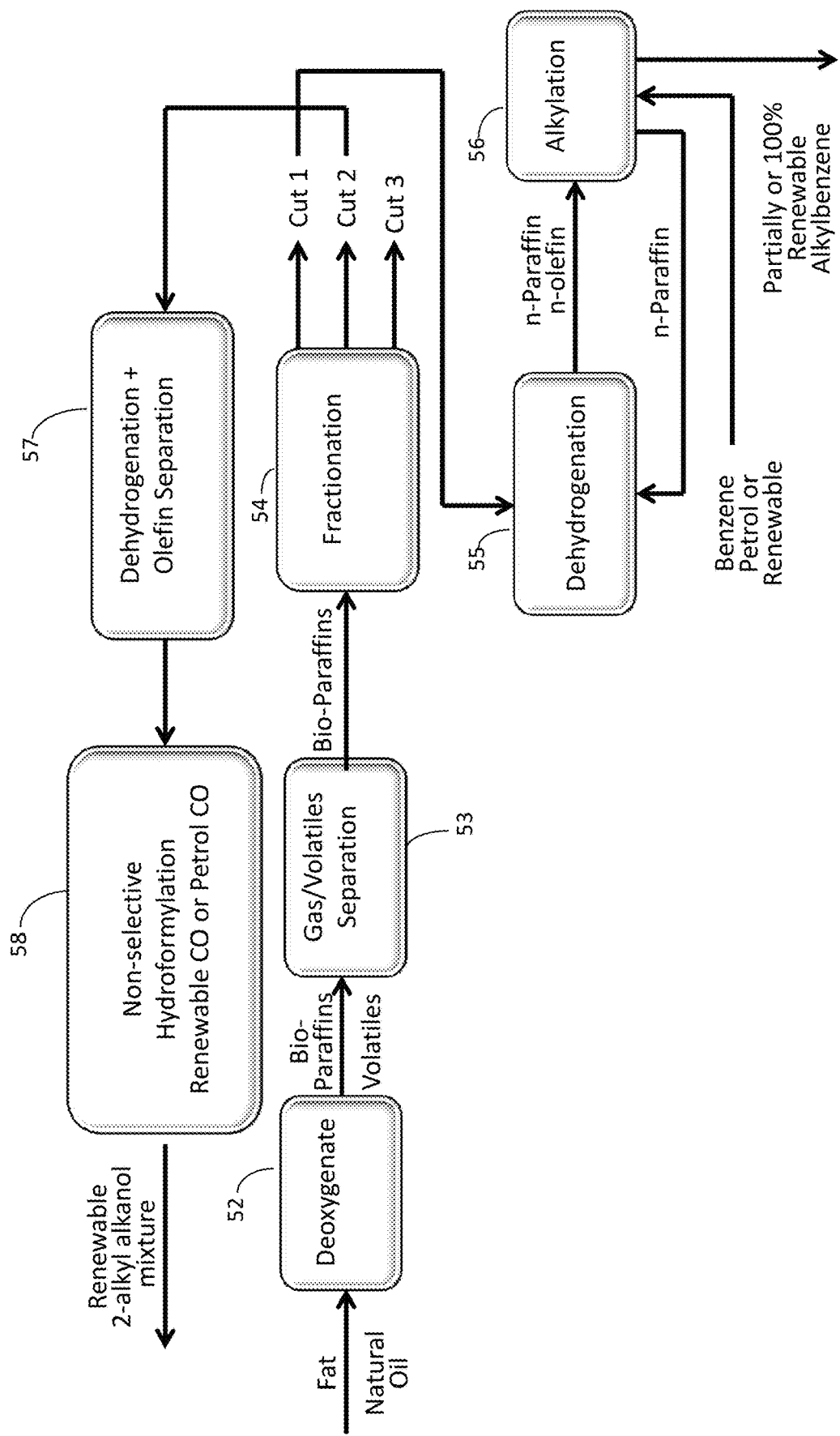
FIG. 7 schematically illustrates a stand-alone system (outside of a conventional kerosene facility) for producing renewable linear paraffins, which are subsequently processed to produce renewable 2-alkyl alkanol and renewable alkylbenzene, FIG. 8 schematically illustrates a stand-alone system (outside of a conventional kerosene facility) to produce renewable linear paraffins, which are subsequently processed to produce renewable 2-alkyl alkanol (with residual cuts of bio-paraffin going to other uses, such as fuel).

A renewable detergent alcohol containing 100% renewable carbon may be produced, for example, if a renewable source of carbon monoxide is used in the preparation of such a detergent alcohol (e.g., the syngas used may be from biomass of any type). A 100%-renewable linear alkyl benzene may be produced. In order to prepare a renewable linear alkyl benzene having 100% renewable carbon content, the alkylation unit may utilize a renewable source of benzene (e.g., from Virent). As shown in FIG. 7, a natural oil is deoxygenated 52, and deoxygenation 52 is followed by a step of removing volatile components and gases 53, to form a purified bio-paraffin. The purified bio-paraffin may be fractionated 54 into any number of cuts, e.g., three cuts. In FIG. 7, a first cut is fed into an alkylbenzene production unit(s) 55, 56 (to dehydrogenate 55 and alkylate 56). The alkylation step 56 may employ a renewable source of benzene to yield a 100% renewable alkylbenzene. In FIG. 7, a second cut is fed into an alcohol production unit(s) 57, 58 (to dehydrogenate the second cut 57, separate out olefins 57, and hydroformylate the olefins 58). The hydroformylation step 58 may employ a renewable source of carbon monoxide to yield a 100% renewable 2-alkyl alkanol mixture.

Detergent Compositions

The detergent compositions described herein may comprise a surfactant in an amount sufficient to provide desired cleaning properties. The detergent compositions may comprise from about 1% to about 75%, by weight of the composition, of a surfactant. The detergent compositions may comprise from about 2% to about 35%, by weight of the composition, of a surfactant. The detergent compositions may comprise from about 5% to about 10%, by weight of the composition, of a surfactant.

The detergent compositions may comprise a renewable surfactant content of at least about 50%, or at least about 70%, or at least about 80%, or at least about 90% (meaning that at least about 50%, or at least about 70%, or at least about 80%, or at least about 90% of the total surfactant in the detergent composition is renewable).

In particular, the detergent compositions may comprise a renewable surfactant produced according to the methods described herein. The detergent compositions may comprise a renewable sulfonated linear alkylbenzene, a renewable sulfated detergent alcohol, and/or a renewable paraffin sulfonate produced according to the method(s) described herein. The detergent compositions may comprise a renewable surfactant produced by the method(s) disclosed herein in combination with natural alcohol sulfates and/or natural alcohol ethoxylated sulfates, such as those derived from the reduction of methyl esters to fatty alcohols.

The detergent compositions may comprise a renewable surfactant produced by the method(s) disclosed herein in combination with a non-renewable surfactant. The non-renewable surfactant may be selected from the group consisting of anionic surfactants, nonionic surfactants, cationic surfactants, zwitterionic surfactants, amphoteric surfactants, ampholytic surfactants, and mixtures thereof.

Non-Renewable Anionic Surfactants

Non-limiting examples of suitable non-renewable anionic surfactants include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The non-renewable anionic surfactant may be a mid-chain branched detersive surfactant, e.g., a mid-chain branched anionic detersive surfactant, such as a mid-chain branched alkyl sulphate and/or a mid-chain branched alkyl benzene sulphonate. Other non-renewable anionic surfactants useful herein are the water-soluble salts of: paraffin sulfonates and secondary alkane sulfonates containing from about 8 to about 24 (and in some examples about 12 to 18) carbon atoms; alkyl glyceryl ether sulfonates, especially those ethers of $C_{8-18}$ alcohols (e.g., those derived from tallow and coconut oil). Mixtures of any of the above-described non-renewable anionic surfactants are also useful. Additional suitable non-renewable anionic surfactants include methyl ester sulfonates and alkyl ether carboxylates.

Non-Renewable Nonionic surfactants

The surfactant may comprise one or more non-renewable nonionic surfactants. The detergent composition may comprise from about 0.1% to about 40% by weight of the composition of a non-renewable nonionic surfactant. The detergent composition may comprise from about 0.3% to about 10% by weight of the composition of a non-renewable nonionic surfactant.

Suitable non-renewable nonionic surfactants useful herein can comprise any conventional nonionic surfactant. These can include, for e.g., alkoxylated nonionic surfactant and amine oxide surfactants. In some examples, the detergent compositions may contain an ethoxylated nonionic surfactant. Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA; $C_{14}$-$C_{22}$ mid-chain branched alkyl alkoxylates, BAE$_x$, wherein x is from 1 to 30; alkylpolysaccharides; specifically alkylpolyglycosides; polyhydroxy fatty acid amides; and ether capped poly(oxyalkylated) alcohol surfactants. Suitable nonionic surfactants also include those sold under the tradename Lutensol® from BASF.

Non-Renewable Cationic Surfactants

The surfactant may comprise one or more non-renewable cationic surfactants. The detergent compositions may comprise from about 0.1% to about 10%, or about 0.1% to about 7%, or about 0.3% to about 5% by weight of the composition, of a surfactant selected from one or more non-renewable cationic surfactants. The detergent compositions of the invention may be substantially free of non-renewable cationic surfactants.

Non-Renewable Zwitterionic Surfactants

Examples of non-renewable zwitterionic surfactants include: derivatives of secondary and tertiary amines, derivatives of heterocyclic secondary and tertiary amines, or derivatives of quaternary ammonium, quaternary phosphonium or tertiary sulfonium compounds. Suitable examples of non-renewable zwitterionic surfactants include betaines, including alkyl dimethyl betaine and cocodimethyl amidopropyl betaine, $C_8$ to $C_{18}$ (for example from $C_{12}$ to $C_{18}$) amine oxides, and sulfo and hydroxy betaines, such as N-alkyl-N,N-dimethylammino-1-propane sulfonate where the alkyl group can be $C_8$ to $C_{18}$.

Non-Renewable Amphoteric Surfactants

Examples of non-renewable amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, or from about 8 to about 18 carbon atoms, and at least one of the aliphatic substituents contains an anionic water-solubilizing group, e.g. carboxy, sulfonate, sulfate. Examples of compounds falling within this definition are sodium 3-(dodecylamino) propionate, sodium 3-(dodecylamino) propane-1-sulfonate, sodium 2-(dodecylamino)ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis (2-hydroxyethyl)-2-sulfato-3-dodecoxypropylamine. Suitable amphoteric surfactants also include sarcosinates, glycinates, taurinates, and mixtures thereof.

Combinations of Surfactants

The detergent compositions may comprise a renewable anionic surfactant and a renewable or non-renewable nonionic surfactant, e.g., $C_{12}$-$C_{18}$ alkyl ethoxylate. The detergent compositions may comprise a renewable alkyl benzene sulfonates (LAS) and another, optionally renewable, anionic surfactant, e.g., $C_{10}$-$C_{18}$ alkyl alkoxy sulfates (AE$_x$S), where x is from 1-30, where the renewable surfactants are produced according to the methods described herein. The detergent compositions may comprise a renewable anionic surfactant and a cationic surfactant, for example, dimethyl hydroxyethyl lauryl ammonium chloride. The detergent compositions may comprise a renewable anionic surfactant and a zwitterionic surfactant, for example, $C_{12}$-$C_{14}$ dimethyl amine oxide.

Adjunct Cleaning Additives

The detergent compositions of the invention may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Enzymes

The detergent compositions described herein may comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a detergent composition, the aforementioned additional enzymes may be present at levels from about 0.00001% to about 2%, from about 0.0001% to about 1% or even from about 0.001% to about 0.5% enzyme protein by weight of the detergent composition.

In one aspect preferred enzymes would include a protease. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii* described in U.S. Pat. No. 6,312,936 B1, U.S. Pat. Nos. 5,679,630, 4,760,025, 7,262,042 and WO09/021867.

(b) trypsin-type or chymotrypsin-type proteases, such as trypsin (e.g., of porcine or bovine origin), including the Fusarium protease described in WO 89/06270 and the chymotrypsin proteases derived from Cellumonas described in WO 05/052161 and WO 05/052146.

(c) metalloproteases, including those derived from *Bacillus amyloliquefaciens* described in WO 07/044993A2.

Preferred proteases include those derived from *Bacillus gibsonii* or *Bacillus lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49

(BLAP with S3T+V4I+A194P+V199M+V205I+L217D)—all from Henkel/Kemira; and KAP (*Bacillus alkalophilus* subtilisin with mutations A230V+S256G+S259N) from Kao.

Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in WO 94/02597, WO 94/18314, WO96/23874 and WO 97/43424, especially the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:
26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp.707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(e) variants described in WO 09/149130, preferably those exhibiting at least 90% identity with SEQ ID NO: 1 or SEQ ID NO:2 in WO 09/149130, the wild-type enzyme from *Geobacillus stearophermophilus* or a truncated version thereof.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

In one aspect, such enzymes may be selected from the group consisting of: lipases, including "first cycle lipases" such as those described in U.S. Pat. No. 6,939,702 B1 and US PA 2009/0217464. In one aspect, the lipase is a first-wash lipase, preferably a variant of the wild-type lipase from Thermomyces lanuginosus comprising one or more of the T231R and N233R mutations. The wild-type sequence is the 269 amino acids (amino acids 23-291) of the Swissprot accession number Swiss-Prot O59952 (derived from Thermomyces lanuginosus (Humicola lanuginosa)). Preferred lipases would include those sold under the tradenames Lipex® and Lipolex®.

In one aspect, other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Enzyme Stabilizing System

The detergent compositions may optionally comprise from about 0.001% to about 10%, in some examples from about 0.005% to about 8%, and in other examples, from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the detergent composition. In the case of aqueous detergent compositions comprising protease, a reversible protease inhibitor, such as a boron compound, including borate, 4-formyl phenylboronic acid, phenylboronic acid and derivatives thereof, or compounds such as calcium formate, sodium formate and 1,2-propane diol may be added to further improve stability.

Builders

The detergent compositions of the present invention may optionally comprise a builder. Built detergent compositions typically comprise at least about 1% builder, based on the total weight of the composition. Liquid detergent compositions may comprise up to about 10% builder, and in some examples up to about 8% builder, of the total weight of the composition. Granular detergent compositions may comprise up to about 30% builder, and in some examples up to about 5% builder, by weight of the composition.

Builders selected from aluminosilicates (e.g., zeolite builders, such as zeolite A, zeolite P, and zeolite MAP) and silicates assist in controlling mineral hardness in wash water, especially calcium and/or magnesium, or to assist in the removal of particulate soils from surfaces. Suitable builders may be selected from the group consisting of phosphates, such as polyphosphates (e.g., sodium tri-polyphosphate), especially sodium salts thereof; carbonates, bicarbonates, sesquicarbonates, and carbonate minerals other than sodium carbonate or sesquicarbonate; organic mono-, di-, tri-, and tetracarboxylates, especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions. Additional suitable builders may be selected from citric acid, lactic acid, fatty acid, polycarboxylate builders, for example, copolymers of acrylic acid, copolymers of acrylic acid and maleic acid, and copolymers of acrylic acid and/or maleic acid, and other suitable ethylenic monomers with various types of additional functionalities. Also suitable for use as builders herein are synthesized crystalline ion exchange materials or hydrates thereof having chain structure and a composition represented by the following general anhydride form: $x(M_2O).ySiO_2.zM'O$ wherein M is Na and/or K, M' is Ca and/or Mg; y/x is 0.5 to 2.0; and z/x is 0.005 to 1.0 as taught in U.S. Pat. No. 5,427,711.

Alternatively, the composition may be substantially free of builder.

Structurant/Thickeners i. Di-benzylidene Polyol Acetal Derivative

The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. In one aspect, the DBPA derivative may comprise a dibenzylidene sorbitol acetal derivative (DBS). Said DBS derivative may be selected from the group consisting of: 1,3:2,4-dibenzylidene sorbitol; 1,3:2,4-di(p-methylbenzylidene) sorbitol; 1,3:2,4-di(p-chlorobenzylidene) sorbitol; 1,3:2,4-di(2,4-dimethyldibenzylidene) sorbitol; 1,3:2,4-di(p-ethylbenzylidene) sorbitol; and 1,3:2,4-di(3,4-dimethyldibenzylidene) sorbitol or mixtures thereof.

ii. Bacterial Cellulose

The fluid detergent composition may also comprise from about 0.005% to about 1% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like. In one aspect, said fibres have cross sectional dimensions of 1.6 nm to 3.2 nm by 5.8 nm to 133 nm. Additionally, the bacterial cellulose fibres have an average microfibre length of at least about 100 nm, or from about 100 to about 1,500 nm. In one aspect, the bacterial cellulose microfibres have an aspect ratio, meaning the average microfibre length divided by the widest cross sectional microfibre width, of from about 100:1 to about 400:1, or even from about 200:1 to about 300:1.

iii. Coated Bacterial Cellulose

In one aspect, the bacterial cellulose is at least partially coated with a polymeric thickener. In one aspect the at least partially coated bacterial cellulose comprises from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

iv. Cellulose Fibers Non-Bacterial Cellulose Derived

In one aspect, the composition may further comprise from about 0.01 to about 5% by weight of the composition of a cellulosic fiber. Said cellulosic fiber may be extracted from vegetables, fruits or wood. Commercially available examples are Avicel® from FMC, Citri-Fi from Fiberstar or Betafib from Cosun.

v. Non-Polymeric Crystalline Hydroxyl-Functional Materials

In one aspect, the composition may further comprise from about 0.01 to about 1% by weight of the composition of a non-polymeric crystalline, hydroxyl functional structurant. Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

vi. Polymeric Structuring Agents

Fluid detergent compositions of the present invention may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon inc under the tradename Carbopol Aqua 30.

vii. Di-Amido-Gellants

In one aspect, the external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. In one aspect, the amido groups are different. In another aspect, the amido functional groups are the same. The di-amido gellant has the following formula:

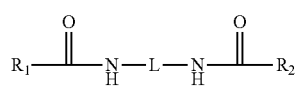

wherein:

$R_1$ and $R_2$ is an amino functional end-group, or even amido functional end-group, in one aspect $R_1$ and $R_2$ may comprise a pH-tuneable group, wherein the pH tuneable amido-gellant may have a pKa of from about 1 to about 30, or even from about 2 to about 10. In one aspect, the pH tuneable group may comprise a pyridine. In one aspect, $R_1$ and $R_2$ may be different. In another aspect, may be the same.

L is a linking moeity of molecular weight from 14 to 500 g/mol. In one aspect, L may comprise a carbon chain comprising between 2 and 20 carbon atoms. In another aspect, L may comprise a pH-tuneable group. In one aspect, the pH tuneable group is a secondary amine. In one aspect, at least one of $R_1$, $R_2$ or L may comprise a pH-tuneable group.

Non-limiting examples of di-amido gellants are:
N,N'-(2S,2'S)-1,1'-(dodecane-1,12-diylbis(azanediyl))bis(3-methyl-1-oxobutane-2,1-diyl)diisonicotinamide

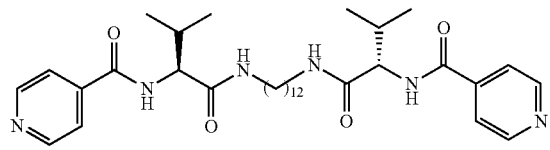

dibenzyl (2S,2'S)-1,1'-(propane-1,3-diylbis(azanediyl))bis(3-methyl-1-oxobutane-2,1-diyl)dicarbamate

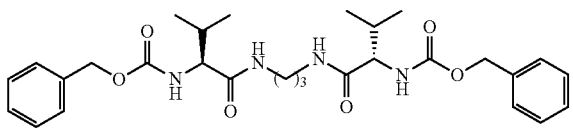

dibenzyl (2S,2'S)-1,1'-(dodecane-1,12-diylbis(azanediyl))bis(1-oxo-3-phenylpropane-2,1-diyl)dicarbamate

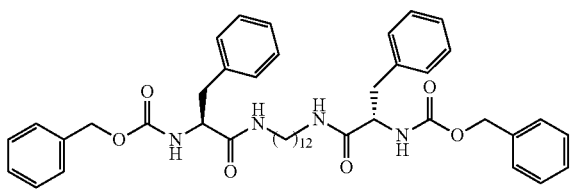

Polymeric Dispersing Agents

The detergent composition may comprise one or more polymeric dispersing agents. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent composition may comprise one or more amphiphilic cleaning polymers such as the compound having the following general structure: bis((C$_2$H$_5$O)(C$_2$H$_4$O)n)(CH$_3$)—N$^+$—C$_x$H$_{2x}$—N$^+$(CH$_3$)—bis((C$_2$H$_5$O)(C$_2$H$_4$O)n), wherein n=from 20 to 30, and x=from 3 to 8, or sulphated or sulphonated variants thereof.

The detergent composition may comprise amphiphilic alkoxylated grease cleaning polymers which have balanced hydrophilic and hydrophobic properties such that they remove grease particles from fabrics and surfaces. The amphiphilic alkoxylated grease cleaning polymers may comprise a core structure and a plurality of alkoxylate groups attached to that core structure. These may comprise alkoxylated polyalkylenimines, for example, having an inner polyethylene oxide block and an outer polypropylene oxide block. Such compounds may include, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The detergent compositions described herein may comprise from about 0.1% to about 10%, and in some examples, from about 0.1% to about 8%, and in other examples, from about 0.1% to about 6%, by weight of the detergent composition, of alkoxylated polyamines.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —(CH$_2$CH$_2$O)$_m$(CH$_2$)$_n$CH$_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. The detergent compositions described herein may comprise from about 0.1% to about 10%, and in some examples, from about 0.25% to about 5%, and in other examples, from about 0.3% to about 2%, by weight of the detergent composition, of alkoxylated polycarboxylates.

Suitable amphilic graft co-polymer preferable include the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan® HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is typically about 6000 and the weight ratio of the polyethylene oxide to polyvinyl acetate is about 40 to 60 and no more than 1 grafting point per 50 ethylene oxide units.

Carboxylate polymer—The detergent compositions of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer—The detergent compositions of the present invention may also include one or more soil release polymers having a structure as defined by one of the following structures (I), (II) or (III):

(I) —[(OCHR$^1$—CHR$^2$)$_a$—O—OC—Ar—CO—]$_d$
(II) —[(OCHR$^3$—CHR$^4$)$_b$—O—OC—sAr—CO—]$_e$
(III) —[(OCHR$^5$—CHR$^6$)$_c$—OR$^7$]$_f$ wherein:
a, b and c are from 1 to 200;
d, e and f are from 1 to 50;
Ar is a 1,4-substituted phenylene;
sAr is 1,3-substituted phenylene substituted in position 5 with SO$_3$Me;
Me is Li, K, Mg/2, Ca/2, Al/3, ammonium, mono-, di-, tri-, or tetraalkylammonium wherein the alkyl groups are C$_1$-C$_{18}$ alkyl or C$_2$-C$_{10}$ hydroxyalkyl, or mixtures thereof;
R$^1$, R$^2$, R$^3$, R$^4$, R$^5$ and R$^6$ are independently selected from H or C$_1$-C$_{18}$ n- or iso-alkyl; and
R$^7$ is a linear or branched C$_1$-C$_{18}$ alkyl, or a linear or branched C$_2$-C$_{30}$ alkenyl, or a cycloalkyl group with 5 to 9 carbon atoms, or a C$_8$-C$_{30}$ aryl group, or a C$_6$-C$_{30}$ arylalkyl group.

Suitable soil release polymers are polyester soil release polymers such as Repel-o-tex polymers, including Repel-o- tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer—The consumer products of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Examples of polymeric dispersing agents are found in U.S. Pat. No. 3,308,067, European Patent Application No. 66915, EP 193,360, and EP 193,360.

Amines

Various amines may be used in the detergent compositions described herein for added removal of grease and particulates from soiled materials. The detergent compositions described herein may comprise from about 0.1% to about 10%, in some examples, from about 0.1% to about 4%, and in other examples, from about 0.1% to about 2%, by weight of the detergent composition, of additional amines Non-limiting examples of amines include, but are not limited to, polyamines, oligoamines, triamines, diamines, pentamines, tetraamines, polyetheramines, or combinations thereof. Specific examples of suitable additional amines include tetraethylenepentamine, triethylenetetraamine, diethylenetriamine, polyetheramines, or a mixture thereof.

Bleaching Agents

The detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the detergent compositions of the present invention may comprise from about 0.1% to about 50% or even from about 0.1% to about 25% bleaching agent by weight of the detergent composition. Examples of suitable bleaching agents include: photobleaches; preformed peracids; sources of hydrogen peroxide; bleach activators having R—(C=O)—L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS).

Bleach Catalysts

The detergent compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Brighteners

Optical brighteners or other brightening or whitening agents may be incorporated at levels of from about 0.01% to about 1.2%, by weight of the composition, into the detergent compositions described herein. Commercial fluorescent brighteners suitable for the present invention can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856, 3,646,015 7,863,236 and its CN equivalent No. 1764714.

In some examples, the fluorescent brightener herein comprises a compound of formula (1):

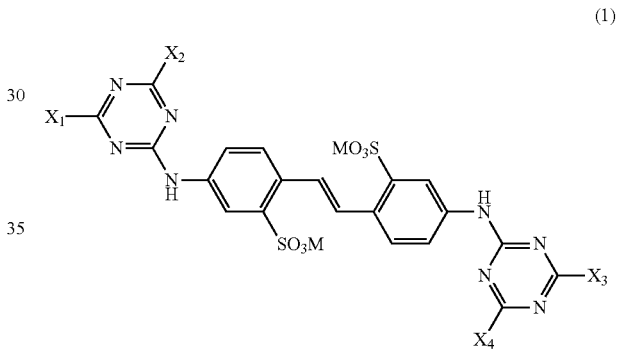

(1)

wherein: $X_1$, $X_2$, $X_3$, and $X_4$ are —N($R^1$)$R^2$, wherein $R^1$ and $R^2$ are independently selected from a hydrogen, a phenyl, hydroxyethyl, or an unsubstituted or substituted $C_1$-$C_8$ alkyl, or —N($R^1$)$R^2$ form a heterocyclic ring, preferably $R^1$ and $R^2$ are independently selected from a hydrogen or phenyl, or —N($R^1$)$R^2$ form a unsubstituted or substituted morpholine ring; and M is a hydrogen or a cation, preferably M is sodium or potassium, more preferably M is sodium.

In some examples, the fluorescent brightener is selected from the group consisting of disodium 4,4'-bis{[4-anilino-6-morpholino-s-triazin-2-yl]-amino}-2,2'-stilbenedisulfonate (brightener 15, commercially available under the tradename Tinopal AMS-GX by Ciba Geigy Corporation), disodium 4,4'-bis{[4-anilino-6-(N-2-bis-hydroxyethyl)-s-triazine-2-yl]-amino}-2,2'-stilbenedisulonate (commercially available under the tradename Tinopal UNPA-GX by Ciba-Geigy Corporation), disodium 4,4'-bis{[4-anilino-6-(N-2-hydroxyethyl-N-methylamino)-s-triazine-2-yl]-amino}-2,2'-stilbenedisulfonate (commercially available under the tradename Tinopal 5BM-GX by Ciba-Geigy Corporation). More preferably, the fluorescent brightener is disodium 4,4'-bis{[4-anilino-6-morpholino-s-triazin-2-yl]-amino}-2,2'-stilbenedisulfonate. The brighteners may be added in particulate form or as a premix with a suitable solvent, for example nonionic surfactant, monoethanolamine, propane diol.

Fabric Hueing Agents

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes such as those described in EP1794275 or EP1794276, or dyes as disclosed in U.S. Pat. No. 7,208,459 B2, and mixtures thereof. In another aspect, suitable small molecule dyes include small molecule dyes selected from the group consisting of C. I. numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in WO2011/98355, WO2011/47987, US2012/090102, WO2010/145887, WO2006/055787 and WO2010/142503. In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenylmethane polymeric colourants, alkoxylated thiophene polymeric colourants, and mixtures thereof.

Preferred hueing dyes include the whitening agents found in WO 08/87497 A1, WO2011/011799 and WO2012/054835. Preferred hueing agents for use in the present invention may be the preferred dyes disclosed in these references, including those selected from Examples 1-42 in Table 5 of WO2011/011799. Other preferred dyes are disclosed in U.S. Pat. No. 8,138,222. Other preferred dyes are disclosed in WO2009/069077.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used).

Encapsulates

The compositions may comprise an encapsulate. The encapsulate may comprise a core, a shell having an inner and outer surface, where the shell encapsulates the core.

The encapsulate may comprise a core and a shell, where the core comprises a material selected from perfumes; brighteners; dyes; insect repellants; silicones; waxes; flavors; vitamins; fabric softening agents; skin care agents, e.g., paraffins; enzymes; anti-bacterial agents; bleaches; sensates; or mixtures thereof; and where the shell comprises a material selected from polyethylenes; polyamides; polyvinylalcohols, optionally containing other co-monomers; polystyrenes; polyisoprenes; polycarbonates; polyesters; polyacrylates; polyolefins; polysaccharides, e.g., alginate and/or chitosan; gelatin; shellac; epoxy resins; vinyl polymers; water insoluble inorganics; silicone; aminoplasts, or mixtures thereof. When the shell comprises an aminoplast, the aminoplast may comprise polyurea, polyurethane, and/or polyureaurethane. The polyurea may comprise polyoxymethyleneurea and/or melamine formaldehyde.

The encapsulate may comprise a core, and the core may comprise a perfume. The encapsulate may comprise a shell, and the shell may comprise melamine formaldehyde and/or cross linked melamine formaldehyde. The encapsulate may comprise a core comprising a perfume and a shell comprising melamine formaldehyde and/or cross linked melamine formaldehyde Suitable encapsulates may comprise a core material and a shell, where the shell at least partially surrounds the core material. At least 75%, or at least 85%, or even at least 90% of the encapsulates may have a fracture strength of from about 0.2 MPa to about 10 MPa, from about 0.4 MPa to about 5 MPa, from about 0.6 MPa to about 3.5 MPa, or even from about 0.7 MPa to about 3 MPa; and a benefit agent leakage of from 0% to about 30%, from 0% to about 20%, or even from 0% to about 5%.

At least 75%, 85% or even 90% of said encapsulates may have a particle size of from about 1 microns to about 80 microns, about 5 microns to 60 microns, from about 10 microns to about 50 microns, or even from about 15 microns to about 40 microns.

At least 75%, 85% or even 90% of said encapsulates may have a particle wall thickness of from about 30 nm to about 250 nm, from about 80 nm to about 180 nm, or even from about 100 nm to about 160 nm.

The core of the encapsulate comprises a material selected from a perfume raw material and/or optionally a material selected from vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil or mixtures thereof; aromatic solvents, including benzene, toluene or mixtures thereof; silicone oils; or mixtures thereof.

The wall of the encapsulate may comprise a suitable resin, such as the reaction product of an aldehyde and an amine. Suitable aldehydes include formaldehyde. Suitable amines include melamine, urea, benzoguanamine, glycoluril, or mixtures thereof. Suitable melamines include methylol melamine, methylated methylol melamine, imino melamine and mixtures thereof. Suitable ureas include, dimethylol urea, methylated dimethylol urea, urea-resorcinol, or mixtures thereof.

Suitable formaldehyde scavengers may be employed with the encapsulates, for example, in a capsule slurry and/or added to a composition before, during, or after the encapsulates are added to such composition.

Suitable capsules can be purchased from Appleton Papers Inc. of Appleton, Wis. USA.

In addition, the materials for making the aforementioned encapsulates can be obtained from Solutia Inc. (St Louis, Mo. U.S.A.), Cytec Industries (West Paterson, N.J. U.S.A.), sigma-Aldrich (St. Louis, Mo. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of N.J. U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA.

Perfumes

Perfumes and perfumery ingredients may be used in the detergent compositions described herein. Non-limiting examples of perfume and perfumery ingredients include, but are not limited to, aldehydes, ketones, esters, and the like. Other examples include various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes may be included at a concentration ranging from about 0.01% to about 2% by weight of the detergent composition.

Dye Transfer Inhibiting Agents

Fabric detergent compositions may also include one or more materials effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Chelating Agents

The detergent compositions described herein may also contain one or more metal ion chelating agents. Suitable molecules include copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl inulins and mixtures thereof. Chelating agents can be present in the acid or salt form including alkali metal, ammonium, and substituted ammonium salts thereof, and mixtures thereof.

Other suitable chelating agents for use herein are the commercial DEQUEST series, and chelants from Monsanto, Akzo-Nobel, DuPont, Dow, the Trilon® series from BASF and Nalco.

The chelant may be present in the detergent compositions disclosed herein at from about 0.005% to about 15% by weight, about 0.01% to about 5% by weight, about 0.1% to about 3.0% by weight, or from about 0.2% to about 0.7% by weight, or from about 0.3% to about 0.6% by weight of the detergent compositions disclosed herein.

Suds Suppressors

Compounds for reducing or suppressing the formation of suds can be incorporated into the detergent compositions described herein. Suds suppression can be of particular importance in the so-called "high concentration cleaning process" as described in U.S. Pat. Nos. 4,489,455, 4,489, 574, and in front-loading style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols.

Additional suitable antifoams are those derived from phenylpropylmethyl substituted polysiloxanes. A suitable antifoam composition comprises:
a) an organomodified silicone comprising one or more 2-phenylpropylmethyl moieties, preferably 1 to 75 mole percent 2-phenylpropylmethyl moieties, more preferably 5 to 50 mole percent 2-phenylpropylmethyl moieties, more preferably 5 to 40 mole percent 2-phenylpropylmethyl moieties, most preferably 15 to 25 mole percent 2-phenylpropylmethyl moieties;
b) silica;
c) a siloxane polymer, said siloxane polymer having a solubility index of greater than about 0.8, more preferably greater than 0.85, more preferably greater than 0.9, more preferably greater than 0.95, greater than 0.98, most preferably from about 0.8 to 1.25 and having a viscosity of from about 0.5 cSt to about 10,000 cSt, of from about 0.5 cSt to about 5,000 cSt, of from about 0.5 cSt to about 1,000 cSt, of from about 2 cSt to about 1,000 cSt, preferably of from about 1 cSt to about 750 cSt, more preferably of from about 1 cSt to about 500 cSt, more preferably of from about 1 cSt to about 100 cSt, most preferably of from about 1 cSt to about 20 cSt; said siloxane polymer having a viscosity that is about 5%, about 10%, about 20%, about 40%, about 50%, about 60%, about 75%, about 90%, about 99%, less than that of said organomodified silicone; and
d) a silicone resin;
the antifoam composition having a viscosity, at a shear rate of 20 sec$^{-1}$ at 25° C., of from about 250 cSt to about 20,000 cSt, preferably of from about 500 cSt to about 10,000 cSt, more preferably of from about 1,000 cSt to about 7,000 cSt, most preferably of from about 1,000 cSt to about 4,000 cSt; a ratio of organomodified silicone to silica of from about 2:1 to about 500:1, preferably of from about 3:1 to about 100:1, more preferably of from about 4:1 to about 70:1, most preferably of from about 5:1 to about 50:1.

The detergent composition may comprise a suds suppressor selected from organomodified silicone polymers with aryl or alkylaryl substituents combined with silicone resin and a primary filler, which is modified silica. The detergent compositions may comprise from about 0.001% to about 4.0%, by weight of the composition, of such a suds suppressor. The detergent composition may comprise a suds suppressor selected from: a) mixtures of from about 80 to about 92% ethylmethyl, methyl(2-phenylpropyl) siloxane; from about 5 to about 14% MQ resin in octyl stearate; and from about 3 to about 7% modified silica; b) mixtures of from about 78 to about 92% ethylmethyl, methyl(2-phenylpropyl) siloxane; from about 3 to about 10% MQ resin in octyl stearate; from about 4 to about 12% modified silica; or c) mixtures thereof, where the percentages are by weight of the anti-foam.

The detergent compositions herein may comprise from 0.1% to about 10%, by weight of the composition, of suds suppressor. When utilized as suds suppressors, monocarboxylic fatty acids, and salts thereof, may be present in amounts of up to about 5% by weight of the detergent composition, and in some examples, from about 0.5% to about 3% by weight of the detergent composition. Silicone suds suppressors may be utilized in amounts of up to about 2.0% by weight of the detergent composition, although higher amounts may be used. Monostearyl phosphate suds suppressors may be utilized in amounts ranging from about 0.1% to about 2% by weight of the detergent composition. Hydrocarbon suds suppressors may be utilized in amounts ranging from about 0.01% to about 5.0% by weight of the detergent composition, although higher levels can be used. Alcohol suds suppressors may be used at a concentration ranging from about 0.2% to about 3% by weight of the detergent composition.

Water-Soluble Film

The compositions of the present invention may also be encapsulated within a water-soluble film. Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. Naturally, different film material and/or films of different thickness may be employed in making the compartments of the present invention. A benefit in selecting different films is that the resulting compartments may exhibit different solubility or release characteristics.

Most preferred film materials are PVA films known under the MonoSol trade reference M8630, M8900, H8779 and PVA films of corresponding solubility and deformability characteristics.

The film material herein can also comprise one or more additive ingredients. For example, it can be beneficial to add plasticisers, for example glycerol, ethylene glycol, diethyleneglycol, propylene glycol, sorbitol and mixtures thereof. Other additives include functional detergent additives to be delivered to the wash water, for example organic polymeric dispersants, etc.

Suds Boosters

If high sudsing is desired, suds boosters such as the $C_{10}$-$C_{16}$ alkanolamides may be incorporated into the detergent compositions at a concentration ranging from about 1% to about 10% by weight of the detergent composition. Some examples include the $C_{10}$-$C_{14}$ monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the detergent composition, to provide additional suds and to enhance grease removal performance.

Conditioning Agents

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from about 0.1% to about 40%, preferably from about 1% to about 30%, more preferably from about 1.5% to about 16% by weight of the composition, from about 1.5% to about 8% in view of providing improved conditioning benefits such as slippery feel during the application to wet hair, softness and moisturized feel on dry hair.

The compositions of the present invention may contain a cationic polymer. Concentrations of the cationic polymer in the composition typically range from about 0.05% to about 3%, or from about 0.075% to about 2.0%, or from about 0.1% to about 1.0%. Suitable cationic polymers will have cationic charge densities of from about 0.5 meq/gm to about 7 meq/gm, at the pH of intended use of the composition, which pH will generally range from about pH 3 to about pH 9. Herein, "cationic charge density" of a polymer refers to the ratio of the number of positive charges on the polymer to the molecular weight of the polymer. The average molecular weight of such suitable cationic polymers will generally be between about 10,000 and 10 million.

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

The composition of the present invention may include a nonionic polymer as a conditioning agent.

Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. The concentration of the silicone conditioning agent typically ranges from about 0.01% to about 10%.

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters.

Hygiene and Malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag+ or nano-silver dispersions.

Fillers and Carriers

Fillers and carriers may be used in the detergent compositions described herein. As used herein, the terms "filler" and "carrier" have the same meaning and can be used interchangeably.

Liquid detergent compositions and other forms of detergent compositions that include a liquid component (such as liquid-containing unit dose detergent compositions) may contain water and other solvents as fillers or carriers. Suitable solvents also include lipophilic fluids, including siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, and mixtures thereof.

Low molecular weight primary or secondary alcohols exemplified by methanol, ethanol, propanol, and isopropanol are suitable. Monohydric alcohols may be used in some examples for solubilizing surfactants, and polyols such as those containing from 2 to about 6 carbon atoms and from 2 to about 6 hydroxy groups (e.g., 1,3-propanediol, ethylene glycol, glycerine, and 1,2-propanediol) may also be used. Amine-containing solvents, such as monoethanolamine, diethanolamine and triethanolamine, may also be used.

The detergent compositions may contain from about 5% to about 90%, and in some examples, from about 10% to about 50%, by weight of the composition, of such carriers. For compact or super-compact heavy duty liquid or other forms of detergent compositions, the use of water may be lower than about 40% by weight of the composition, or lower than about 20%, or lower than about 5%, or less than about 4% free water, or less than about 3% free water, or less than about 2% free water, or substantially free of free water (i.e., anhydrous).

For powder or bar detergent compositions, or forms that include a solid or powder component (such as powder-containing unit dose detergent composition), suitable fillers may include, but are not limited to, sodium sulfate, sodium chloride, clay, or other inert solid ingredients. Fillers may also include biomass or decolorized biomass. Fillers in granular, bar, or other solid detergent compositions may comprise less than about 80% by weight of the detergent composition, and in some examples, less than about 50% by weight of the detergent composition. Compact or supercompact powder or solid detergent compositions may comprise less than about 40% filler by weight of the detergent composition, or less than about 20%, or less than about 10%.

For either compacted or supercompacted liquid or powder detergent compositions, or other forms, the level of liquid or solid filler in the product may be reduced, such that either the same amount of active chemistry is delivered to the wash liquor as compared to noncompacted detergent compositions, or in some examples, the detergent composition is more efficient such that less active chemistry is delivered to the wash liquor as compared to noncompacted compositions. For example, the wash liquor may be formed by contacting the detergent composition to water in such an amount so that the concentration of detergent composition in the wash liquor is from above 0 g/l to 6 g/l. In some examples, the concentration may be from about 0.5 g/l to about 5 g/l, or to about 3.0 g/l, or to about 2.5 g/l, or to about 2.0 g/l, or to about 1.5 g/l, or from about 0 g/l to about 1.0 g/l, or from about 0 g/l to about 0.5 g/l. These dosages are not intended to be limiting, and other dosages may be used that will be apparent to those of ordinary skill in the art.

Buffer System

The detergent compositions described herein may be formulated such that, during use in aqueous cleaning operations, the wash water will have a pH of between about 7.0 and about 12, and in some examples, between about 7.0 and about 11. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

The detergent compositions herein may comprise dynamic in-wash pH profiles. Such detergent compositions may use wax-covered citric acid particles in conjunction with other pH control agents such that (i) about 3 minutes after contact with water, the pH of the wash liquor is greater than 10; (ii) about 10 minutes after contact with water, the pH of the wash liquor is less than 9.5; (iii) about 20 minutes after contact with water, the pH of the wash liquor is less than 9.0; and (iv) optionally, wherein, the equilibrium pH of the wash liquor is in the range of from about 7.0 to about 8.5.

Catalytic Metal Complexes

The detergent compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof.

Other Adjunct Ingredients

A wide variety of other ingredients may be used in the detergent compositions herein, including other active ingredients, carriers, hydrotropes, processing aids, dyes or pigments, solvents for liquid formulations, and solid or other liquid fillers, erythrosine, colliodal silica, waxes, probiotics, surfactin, aminocellulosic polymers, Zinc Ricinoleate, perfume microcapsules, rhamnolipids, sophorolipids, glycopeptides, methyl ester sulfonates, methyl ester ethoxylates, sulfonated estolides, cleavable surfactants, biopolymers, silicones, modified silicones, aminosilicones, deposition aids, locust bean gum, cationic hydroxyethylcellulose polymers, cationic guars, hydrotropes (especially cumenesulfonate salts, toluenesulfonate salts, xylenesulfonate salts, and naphalene salts), antioxidants, BHT, PVA particle-encapsulated dyes or perfumes, pearlescent agents, effervescent agents, color change systems, silicone polyurethanes, opacifiers, tablet disintegrants, biomass fillers, fast-dry silicones, glycol distearate, hydroxyethylcellulose polymers, hydrophobically modified cellulose polymers or hydroxyethylcellulose polymers, starch perfume encapsulates, emulsified oils, bisphenol antioxidants, microfibrous cellulose structurants, properfumes, styrene/acrylate polymers, triazines, soaps, superoxide dismutase, benzophenone protease inhibitors, functionalized TiO2, dibutyl phosphate, silica perfume capsules, and other adjunct ingredients, silicate salts (e.g., sodium silicate, potassium silicate), choline oxidase, pectate lyase, mica, titanium dioxide coated mica, bismuth oxychloride, and other actives.

The detergent compositions described herein may also contain vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine, and minoxidil.

The detergent compositions of the present invention may also contain pigment materials such as nitroso, monoazo, disazo, carotenoid, triphenyl methane, triaryl methane, xanthene, quinoline, oxazine, azine, anthraquinone, indigoid, thionindigoid, quinacridone, phthalocianine, botanical, and natural colors, including water soluble components such as those having C.I. Names. The detergent compositions of the present invention may also contain antimicrobial agents.

Processes of Making Detergent Compositions

The detergent compositions of the present invention can be formulated into any suitable form and prepared by any process chosen by the formulator.

Methods of Use

The present invention includes methods for cleaning soiled material. As will be appreciated by one skilled in the art, the detergent compositions of the present invention are suited for use in laundry pretreatment applications, laundry cleaning applications, and home care applications.

Such methods include, but are not limited to, the steps of contacting detergent compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the detergent compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry detergent composition in accord with the invention. An "effective amount" of the detergent composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The detergent compositions herein may be used for laundering of fabrics at reduced wash temperatures. These methods of laundering fabric comprise the steps of delivering a laundry detergent composition to water to form a wash liquor and adding a laundering fabric to said wash liquor, wherein the wash liquor has a temperature of from about 0° C. to about 20° C., or from about 0° C. to about 15° C., or from about 0° C. to about 9° C. The fabric may be contacted to the water prior to, or after, or simultaneous with, contacting the laundry detergent composition with water.

Another method includes contacting a nonwoven substrate, which is impregnated with the detergent composition, with a soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SON-TARA® by DuPont and POLYWEB® by James River Corp.

Hand washing/soak methods, and combined handwashing with semi-automatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the detergent composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the detergent composition onto soiled dishes, tableware, silverware, or other kitchenware, then hand scrubbing, wiping, or rinsing the soiled dishes, tableware, silverware, or other kitchenware. In some examples, an effective amount of detergent composition for hand dishwashing is from about 0.5 ml. to about 20 ml. diluted in water.

Packaging for the Compositions

The detergent compositions described herein can be packaged in any suitable container including those constructed from paper, cardboard, plastic materials, and any suitable laminates.

Multi-Compartment Pouch Additive

The detergent compositions described herein may also be packaged as a multi-compartment detergent composition.

ANALYSIS METHODS AND EXAMPLES

Assessment of the Biobased Content of Materials

A suitable method to assess materials derived from renewable resources is through ASTM D6866, which allows the determination of the biobased content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide.

The application of ASTM D6866 to derive a "biobased content" is built on the same concepts as radiocarbon dating, but without the use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample.

The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), or at least about 99 pMC, for example, about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biobased content result is derived by assigning 100% equal to 107.5 pMC and 0% equal to 0 pMC. In this regard, a sample measuring 99 pMC will give an equivalent biobased content result of 93%.

Assessment of the materials described herein are done in accordance with ASTM D6866, particularly with Method B. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

GC Sample Preparation

In order to identify the various products of the process, derivatization is necessary since analysis of oils themselves or fatty acid intermediates is not feasible by direct analysis on this column. All data reported herein on the Agilent Technologies Gas Chromatograph 7890A instrument are in area %.

Derivatized samples are prepared by drying a 1 ml sample of the reactor effluent over $MgSO_4$, filtering, and adding 20 μl of resultant to a vial followed by 1.5 ml of 14% $BF_3$ in MeOH and heating to 65° C. for 30 minutes. 1.5 ml of water is then added followed by 2.0 ml of hexane. This is then shaken and the organic layer is allowed to separate. Once separated, the top organic layer is dried through a $MgSO_4$ plug into a GC vial. The resultant sample is analyzed by GC using the following: Agilent Technologies Gas Chromatograph 7890A equipped with a split/splitless injector and FID, J&W Scientific capillary column DB-1HT, 30 meter, 0.25 mm id, 0.1 μm film thickness cat #1221131, EMD Chemicals HPLC grade Chloroform, cat # EM-X1058-1 or equivalent, 2 ml GC autosampler vials with screw tops, or equivalent.

GC Parameters:

Carrier Gas: Helium
  Column Head Pressure: 18.5 psi
  Flows: Column Flow @1.6 ml/min
  Split Vent @19.2 ml/min
  Septum Purge @3 ml/min.
  Injection: Agilent Technologies 7693 Series Autosampler, 10 ul syringe, 1 ul injection
  Injector Temperature: 275° C.
  Detector Temperature: 340° C.
  Oven Temperature Program: initial 70° C. hold 1 min; rate 10° C./min; final 320° C. hold 5 min Another procedure to analyze for impurities in the renewable paraffin is 2D GCMS. This system is well known in the analytical literature as providing a way to separate complex compositions and to identify by mass spectroscopy the type of materials separated.

2D GCMS Analysis Procedure:

2D-GC/FID—Relatively Quantitative Comparison

Equipment: Leco Comprehensive 2-dimensional Gas Chromatograph, Agilent 7890 GC System (Leco modified) w/split/splitless injector & flame ionization detector (FID), Leco Secondary oven, Leco LN2 modulator and controller, CTC Combi-PAL Autosampler (or equivalent), Columns: Supelco Gamma DEX 120 (30 m×0.25 mm ID×0.25 um df), Deactivated transfer line Restek 'Siltek' (0.66 m×0.25 mm ID), Varian VF-5 ms (2 m×0.15 mm ID×0.15 um df). In the following configuration:

| # | Type | Location | Length (m) | Int. Diameter (μ) | Max Temp (° C.) | Film Thickness (μ) | Phase |
|---|------|----------|-----------|-------------------|-----------------|--------------------|-------|
| 1 | Inlet | Front | | | | | |
| 2 | Capillary | GC Oven | 30.000 | 250.00 | 235.0 | 0.25 | G-DEX 120 |
| 3 | Capillary | Modulator | 0.660 | 250.00 | 350.0 | 0.00 | Deactivated FS |
| 4 | Capillary | Secondary Oven | 1.770 | 150.00 | 360.0 | 0.15 | VF-5 ms |
| 5 | Capillary | Detector or MS Transfer Line | 0.330 | 150.00 | 360.0 | 0.15 | VF-5 ms |

Sample Preparation: Dilute sample 100:1 in dichlormethane (DCM) eg. as follows: Pipette 10 uL of paraffin or kerosene sample into 2 mL GC vial, Pipette 990 uL DCM into same GC vial, Cap with septa seal and mix (vortex mixer) 20 seconds.

Instrument Parameters: Carrier Gas: Helium @ 1.1 mL/min (constant flow mode), Injection: 1 uL Split 50:1 @200° C., Primary Oven: Initial 35° C. hold 2 min; Ramp 1—1° C./min to 200° C.; Ramp 2—5° C./min to 220° C. Secondary Oven: +10° C. offset tracking primary oven. Modulator Temp: +25° C. offset tracking primary oven. Modulator Program: Entire run—18.5 second modulation period; Hot pulse time—8.75 seconds; Cool time between stages 0.5 seconds. Detector: (FID) Temp. 300° C.; Data collection rate: 200 Hz; Makeup 25 mL/min Nitrogen (Makeup+column); Hydrogen: 40 mL/min; Air: 450 mL/min.

2D-GC/TOFMS—Qualitative Composition

Equipment: Leco Pegasus 4D—Comprehensive 2-D GC+Time-of-Flight Mass Spectrometer; Leco Comprehensive 2-dimensional Gas Chromatograph; Agilent 7890 GC System (Leco modified) w/split/splitless injector & flame ionization detector (FID); Leco Secondary oven; Leco LN2 modulator and controller; CTC Combi-PAL Autosampler (or equivalent); Columns: Supelco Gamma DEX 120 (30 m×0.25 mm ID×0.25 um df), Deactivated transfer line 'Restek Siltek' (0.4 m×0.25 mm ID), Restek rxi-XLB (2.1 m×0.18 mm ID×0.18 um df). In the following configuration:

| # | Type | Location | Length (m) | Int. Diameter (μ) | Max Temp (° C.) | Film Thickness (μ) | Phase |
|---|---|---|---|---|---|---|---|
| 1 | Inlet | Front | | | | | |
| 2 | Capillary | GC Oven | 30.000 | 250.00 | 250.0 | 0.25 | G-DEX 120 |
| 3 | Capillary | Modulator | 0.400 | 250.00 | 360.0 | 0.00 | Deactivated FS |
| 4 | Capillary | Secondary Oven | 2.000 | 180.00 | 360.0 | 0.18 | rxi-XLB |
| 5 | Capillary | Detector or MS Transfer Line | 0.100 | 180.00 | 360.0 | 0.18 | rxi-XLB |
| 6* | Detector | TOF | | | | | |

Sample Preparation: Dilute sample 100:1 in dichlormethane (DCM) eg. as follows: Pipette 10 uL of paraffin or kerosene sample into 2 mL GC vial, Pipette 990 uL DCM into same GC vial, Cap with septa seal and mix (vortex mixer) 20 seconds.

Instrument Parameters: Carrier Gas: Helium @ 1.1 mL/min (constant flow mode), Injection: 1 uL Split 50:1 @200° C., Primary Oven: Initial 35° C. hold 2 min; Ramp 1—1° C./min to 200° C.; Ramp 2—5° C./min to 220° C. Secondary Oven: +10° C. offset tracking primary oven. Modulator Temp: +25° C. offset tracking primary oven. Modulator Program: Entire run—18.5 second modulation period; Hot pulse time—8.75 seconds; Cool time between stages 0.5 seconds. Detector: (TOF-MS): Tranfer line Temperature: 250° C., Data collection rate: 200 spectra/second, Electron Energy: −70V, Mass Range 45-450 m/z, Solvent Delay: 150 seconds, Source Temperature: 210° C.

HT-GC/FID—High Temp Fast GC for High Boilers (FFE & Residual Triglyceride)

Equipment: Agilent 7890 GC System w/split/splitless injector & flame ionization detector (FID); Agilent 7693 Autosampler (or equivalent); Columns: Agilent J&W DB1-HT (5 m×0.25 mm ID×0.1 um df—cut from 30 m Column #122-1131).

Sample Preparation: Dilute sample 100:1 in dichlormethane (DCM) eg. as follows: Pipette 10 uL of paraffin or kerosene sample into 2 mL GC vial, Pipette 990 uL DCM into same GC vial, Cap with septa seal and mix (vortex mixer) 20 seconds.

Instrument Parameters: Carrier Gas: Helium @ 1.4 mL/min (constant flow mode); Injection: 1 uL Pulsed Split 25:1 @ 325° C., Pressure Pulse: 10 psi until 0.15 min Oven Program: Initial 40° C. hold 0.5 min; Ramp 1—40° C./min to 380° C. hold 3 min. Detector: (FID) Temp. 380° C., Data collection rate: 50 Hz, Makeup 25 mL/min Helium, Hydrogen: 40 mL/min, Air: 450 mL/min.

Flow Cat Reactor General Procedure for EXAMPLES 1-2:

Catalyst is added to the ½" FlowCat reaction tube to give a bed length of 4 inches. The reaction tube is installed on a HEL E961 FlowCat®. The system is purged 3 times with 300 PSI $N_2$ followed by 3 times 300 PSI $H_2$. The system is pressurized to the operating pressure with $H_2$ and heated to the operation temperature over 2 hours under operating $H_2$ flow. The catalyst is held under these conditions overnight to activate. Experiments are conducted under conditions outlined in TABLE 1 using feed of coconut oil or palm kernel oil, neat or diluted with hexane as carrier. Non-limiting examples 1 and 2 shown below are result of feed of coconut oil.

TABLE 1

Examples 1 and 2.

| Example | 1 | 2 |
|---|---|---|
| $H_2$ Flow ml/min | 200 | 200 |
| Liquid Flow ml/min | 0.21 | 0.21 |
| Catalyst Trading Company, ltd. | Haldor Topsoe | Albemarle |
| Catalyst ID | TK-527 (NiMo) | KF-841 (PS-NiMo) |
| Temp ° C. | 400 | 320 |
| Press PSI | 515 | 750 |
| GHSV | 924 | 924 |
| LHSV | 0.97 | 0.97 |
| % linear paraffin | 93.3 | 98.0 |
| % ester (see method) | 0.0 | 0.0 |
| % total of branched, cyclic and aromatics | 5.0 | 1.6 |
| % C18+ | 1.67 | 0.43 |
| Ester/Par | 0.00 | 0.00 |
| Even/Odd | 3.24 | 0.53 |

TABLE 2

Chain Composition of Example 1 vs. Example 2

| Example Linear Chain Length | 1 % composition | 2 % Composition |
|---|---|---|
| C8 | 4.715 | 2.494 |
| C9 | 1.237 | 3.142 |
| C10 | 4.700 | 2.124 |
| C11 | 9.362 | 27.588 |
| C12 | 33.203 | 15.645 |
| C13 | 4.173 | 11.845 |
| C14 | 13.127 | 6.105 |
| C15 | 3.090 | 8.804 |
| C16 | 8.867 | 4.325 |
| C17 | 3.062 | 11.080 |
| C18 | 7.800 | 4.834 |
| other | 1.67 | 0.43 |
| lin par % | 93.3 | 98.0 |
| Even/Odd | 3.24 | 0.53 |

Flow Reactor General Procedure for EXAMPLES 4-10:

Catalyst is added to the ½" 316 stainless steel reaction tube to give a bed length of 9 inches. The reaction tube is installed in a flow reactor system built from: Brooks Instruments Mass Flow Controller, Model SLA5850S1CAB1B2A1, S/N 0109120406387001; Brooks Instruments Pressure Controller, Model SLA5820A1CDH1B1A1, S/N 01B20290457; Brooks Instruments Model 0254AA1B21A four-channel power supply, readout and set point controller, S/N 011030457589001; J-Kem Scientific 4 channel temperature controller; Applied Test Systems Inc Series 3210 Furnace/Oven, Watts 1100, Volts 115, Amps/Zone 9.6, Conn 1-2286-1, with 9 inch heating zone, Max Temp 1650° F., Date January 2010, Serial #09-5152.

The system is purged 3 times with 300 PSI $N_2$ followed by 3 times 300 PSI $H_2$. The system is pressurized to the operating pressure with $H_2$ and heated to the operation temperature over 2 hours under operating $H_2$ flow. The catalyst is held under these conditions overnight to activate. Liquid feed—palm kernel oil, coconut oil, or blends with hexane diluent—is pumped through the system via HPLC pump. Nonlimiting examples 3-9 use coconut oil. Experiments are conducted under conditions outlined in Table 3 with results reported below. The GC analysis method described above is used for examples 3-9.

TABLE 3

Examples 3 through 9

| EXAMPLE | 3 | 4 | 5 | 6 | 7 | 8 | 9 |
|---|---|---|---|---|---|---|---|
| $H_2$ Flow (ml/min) | 500 | 400 | 500 | 450 | 450 | 450 | 450 |
| Liquid Flow (ml/min) | 0.6 | 0.4 | 0.5 | 0.8 | 0.3 | 0.55 | 0.55 |
| Catalyst Trading Company, ltd. | Haldor Topsoe | Haldor Topsoe | Haldor Topsoe | Haldor Topsoe | Haldor Topsoe | Haldor Topsoe | Haldor Topsoe |
| Catalyst | TK-527 (NiMo) | TK-527 (NiMo) | TK-527 (NiMo) | TK-527 (NiMo) | TK-527 (NiMo) | TK-527 (NiMo) | TK-527 (NiMo) |
| Temp ° C. | 406 | 406 | 406 | 385 | 385 | 386 | 367 |
| $H_2$ Pres (PSI) | 480 | 480 | 480 | 500 | 500 | 500 | 500 |
| GHSV | 1600 | 1280 | 1600 | 1440 | 1440 | 1440 | 1440 |
| LHSV | 1.92 | 1.28 | 1.6 | 2.56 | 0.96 | 1.76 | 1.76 |
| % Linear Paraffin | 91.83 | 92.22 | 92.36 | 92.57 | 94.29 | 95.14 | 97.32 |
| % Ester | 0.34 | 0.00 | 0.00 | 0.54 | 0.00 | 0.00 | 0.00 |
| % total of branched, cyclic and aromatics | 5.56 | 6.61 | 6.00 | 4.43 | 5.10 | 3.06 | 1.66 |
| % C18+ | 1.92 | 1.14 | 1.63 | 2.47 | 0.61 | 1.79 | 1.02 |
| Ester/Par | 0.00 | 0.00 | 0.00 | 0.01 | 0.00 | 0.00 | 0.00 |
| Even/Odd | 5.64 | 4.86 | 5.63 | 3.47 | 4.37 | 3.76 | 2.42 |

The chain composition can be modified depending on the choice of catalyst, such as Ni/Mo or Ni/Mo sulfurized, leading to various ratios of even and odd chains, from increased even to odd ratios to decreased even to odd ratios. This can be beneficial depending on the selection of chain cuts desired by the end user of the surfactant, e.g., the renewable linear alkyl benzene or the renewable detergent alcohol of the invention.

The same procedure as in examples 3-9 is followed for examples 10-11. Examples 10-11 use coconut oil as feed. Experiments are conducted under conditions outlined in Table 4 for this catalyst with results reported below. The GC analysis method described above is used for examples 10-11.

TABLE 4

Pd/Alumina and Pd/Carbon data for examples 10-11.

| EXAMPLE | 10 | 11 |
|---|---|---|
| Supplier | Jm/Alfa Aesar | Aldrich |
| Catalyst | 5% Pd/Al | 5% Pd/C |
| $H_2$ Flow (ml/min) | 50 | 100 |
| Liquid Flow (ml/min) | 0.6 | 0.4 |
| Temp ° C. | 403 | 330 |
| $H_2$ Pres (PSI) | 300 | 300 |
| GHSV | 240 | 240* |
| LHSV | 1.92 | 192* |
| % Linear Paraffin | 89.40 | 98.52 |
| % Ester | 6.652 | 0.36 |
| % total of branched, cyclic, aromatics | 7.572 | 1.11 |
| % C18+ | 3.029 | 0.27 |
| Ester/Par | 0.142 | 0.00 |
| Even/Odd | 0.003 | 0.01 |

*not measured but predicted to be similar to example 10

As shown in Table 5, by using 2D GCMS analysis, more detail on impurities may be obtained than via standard GC analysis on Examples 1, 2, and 9. Purity of the renewable linear paraffin is shown to be greater than 90%.

TABLE 5 analysis of samples via 2D GCMS:
2D-GC/FID Results

| Example | 1 | 2 | 9 |
|---|---|---|---|
| Paraffin | 99.4 | 94.4 | 99.8 |
| linear | 98.9 | 94.1 | 98.9 |
| branched | 0.5 | 0.3 | 0.9 |
| Olefin/Cyclic | 0.5 | 5.4 | 0.2 |
| Alcohol | 0 | 0.1 | 0 |
| Aldehyde | 0 | 0 | 0 |
| Ester | 0.1 | 0.1 | 0 |

Example 12: Renewable linear alkyl benzene and renewable detergent alcohol production using the renewable linear paraffin product of example 3. The renewable linear paraffin product of Example 3 is provided to a gas removal unit (FIG. 2, 9) to remove volatile gases and short chain hydrocarbons and then is provided to a standard petroleum refining fractionation unit (FIG. 2, 10) to provide three cuts of paraffins—C10-13 (cut 1), C14-16 (cut 2), and C17-C18 (cut 3). Cut 1 is sent to a dehydrogenation unit (FIG. 2, 13) and then to an alkylation unit (FIG. 2, 14), where it is alkylated with benzene to provide a renewable (partially, petrol-based benzene) alkyl benzene. Procedures to remove benzene and heavy distillate from the renewable alkyl benzene product are known to one skilled in the art. Cut 2 is sent to another dehydrogenation unit (FIG. 2, 15) followed by the step of olefin absorptive separation to provide a high purity renewable linear olefin mixture, which is further subjected to a selective hydroformylation catalyst in a hydroformylation unit (FIG. 2, 16) to provide a renewable, mostly linear, detergent alcohol. Optionally, cut 3 is sent to a sulfoxidation unit (FIG. 2a, 17) to provide a renewable paraffin sulfonate surfactant.

Example 13: Renewable linear alkyl benzene and renewable detergent alcohol production using the renewable linear paraffin product of example 9. The renewable linear paraffin product of Example 9 is provided to gas removal unit (FIG. 2, 9) to remove the volatile gases and short chain hydrocarbons and then is provided to a standard petroleum refining fractionation unit (FIG. 2, 10) to provide three cuts of paraffins—C10-13 (cut 1), C14-16 (cut 2), and C17-C18 (cut 3). Cut 1 is sent to a dehydrogenation unit (FIG. 2, 13) and then to an alkylation unit (FIG. 2, 14), where it is alkylated with benzene to provide a renewable (partially, petrol-based benzene) alkyl benzene. Procedures to remove benzene and heavy distillate from the renewable alkyl benzene product are known to one skilled in the art. Cut 2 is sent to another dehydrogenation unit (FIG. 2, 15) followed by the step of olefin absorptive separation to provide a high purity renewable linear olefin mixture, which is further subjected to a non-selective hydroformylation catalyst in a hydroformylation unit (FIG. 2, 16) to provide a renewable detergent alcohol mixture with greater than 25% 2-alkyl alkanol. Optionally, cut 3 is sent to a sulfoxidation unit (FIG. 2a, 17) to provide a renewable paraffin sulfonate surfactant.

Example 14: Renewable linear alkyl benzene sulfonate. The renewable linear alkyl benzene product of example 13 is sulfonated in a standard falling film sulfonator unit and subsequently neutralized providing a renewable linear alkyl benzene sulfonate surfactant.

Example 15: Renewable detergent alcohol sulfate containing greater than 25% 2-alkyl alkanol sulfate. The renewable detergent alcohol of example 13 is sulfated under standard conditions and neutralized.

Example 16: Blends of renewable alkyl benzene sulfonate and renewable detergent alcohol sulfate. The renewable linear alkyl benzene sulfonate of example 14 is blended with the renewable detergent alcohol sulfate of example 15 in weight ratios from about 1:99 to about 99:1 to provide a renewable surfactant mixture.

Example 17: Renewable ethoxylated sulfate. The renewable alcohol of example 12 is ethoxylated using standard procedures to an ethoxylate average of about 1.8 and subsequently sulfated in a standard falling film sulfonation procuess to provide a renewable ethoxylate sulfate that is substantially linear.

Example 18: Blends of example 14, 15 and 17. The renewable surfactants of example 14, 15 and 17 are blended in various ratios to provide three-component blends of the renewable surfactant mixtures.

Example 19: Blends of example 15 and standard natural alcohol ethoxylated sulfates. Natural alcohol ethoxylated sulfates with an average degree of ethoxylation of about 3 are blended with example 15 to provide a renewable surfactant mixture.

Example 20

| | Liquid Detergent A (wt %) | Liquid Detergent B (wt %) | Liquid Detergent C (wt %) | Liquid Detergent D (wt %) |
|---|---|---|---|---|
| AES $C_{12-15}$ alkyl ethoxy (1.8) sulfate | 1-12 | 0 | 1-12 | 1-12 | 1-12 |
| Alkyl benzene sulfonate[2] | 1-5 | 0 | 1-5 | 1-5 | 1-10 |
| Sodium formate | 2.66 | 2.66 | 2.66 | 2.66 | 0.11 |
| Calcium formate | — | — | — | — | 0.097 |
| Sodium hydroxide | 0.21 | 0.21 | 0.21 | 0.21 | 0.68 |
| Monoethanolamine (MEA) | 1.65 | 1.65 | 1.65 | 1.65 | 2.80 |
| Diethylene glycol (DEG) | 4.10 | 4.10 | 4.10 | 4.10 | 1.23 |
| Propylene glycol | — | — | — | — | 8.39 |
| AE9[3] | 0.40 | 0.40 | 0.40 | 0.40 | — |
| C16AE7 | 3.15 | 3.15 | 3.15 | 3.15 | — |
| NI 24-9[13] | — | — | — | — | 0.97 |
| Renewable Surfactant[11] | 5-20 | 15-30 | 1-5 | 10-20 | 1-5 |
| Chelant[4] | 0.18 | 0.18 | 0.18 | 0.18 | 0.29 |
| Citric Acid | 1.70 | 1.70 | 1.70 | 1.70 | 2.83 |
| $C_{12-18}$ Fatty Acid | 1.47 | 1.47 | 1.47 | 1.47 | 1.09 |
| Borax | 1.19 | 1.19 | 1.19 | 1.19 | 2.00 |
| Ethanol | 1.44 | 1.44 | 1.44 | 1.44 | 1.47 |

-continued

| | Liquid Detergent A (wt %) | Liquid Detergent B (wt %) | Liquid Detergent C (wt %) | Liquid Detergent D (wt %) |
|---|---|---|---|---|
| Ethoxylated Polyethyleneimine[1] | 1.35 | 1.35 | 1.35 | 1.85 |
| Amphiphilic alkoxylated grease cleaning polymer[12] | — | — | — | 0.940 |
| A compound having the following general structure: bis$((C_2H_5O)(C_2H_4O)n)(CH_3)$—$N^+$—$C_xH_{2x}$—$N^+(CH_3)$—bis$((C_2H_5O)(C_2H_4O)n)$, wherein n = from 20 to 30, and x = from 3 to 8, or sulphated or sulphonated variants thereof | 0.40 | 0.40 | 0.40 | 1.40 |
| 1,2-Propanediol | 2.40 | 2.40 | 2.40 | 2.40 | — |
| Protease (54.5 mg active/g)[9] | 0.89 | 0.89 | 0.89 | 0.89 | 0.95 |
| Mannanase: Mannaway ® (25.6 mg active/g)[5] | 0.04 | 0.04 | 0.04 | 0.04 | — |
| Xyloglucanase: Whitezyme ® (20 mg active/g)[14] | — | — | — | — | 0.04 |
| Cellulase: Carezyme ™ (11.63 mg active/g)[14] | — | — | — | — | 0.10 |
| Amylase: Natalase ® (29 mg active/g)[5] | 0.14 | 0.14 | 0.14 | 0.14 | 0.34 |
| Fluorescent Whitening Agents[10] | 0.10 | 0.10 | 0.10 | 0.10 | 0.15 |
| Water, perfume, dyes & other components | | Balance | | | Balance |

[1]Polyethyleneimine (MW = 600) with 20 ethoxylate groups per —NH.
[2]Linear alkylbenzenesulfonate having an average aliphatic carbon chain length $C_{11}$-$C_{12}$ supplied by Stepan, Northfield, Illinois, USA
[3]AE9 is $C_{12-13}$ alcohol ethoxylate, with an average degree of ethoxylation of 9, supplied by Huntsman, Salt Lake City, Utah, USA
[4]Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark
[5]Natalase ®, Mannaway ® are all products of Novozymes, Bagsvaerd, Denmark.
[6]Proteases may be supplied by Genencor International, Palo Alto, California, USA (e.g. Purafect Prime ®) or by Novozymes, Bagsvaerd, Denmark (e.g. Liquanase ®, Coronase ®).
[10]Suitable Fluorescent Whitening Agents are for example, Tinopal ® AMS, Tinopal ® CBS-X, Sulphonated zinc phthalocyanine Ciba Specialty Chemicals, Basel, Switzerland
[11]Renewable surfactant of Example 14, 15, 16, 17, 18, or 19.
[12]Amphiphilic alkoxylated grease cleaning polymer is a polyethyleneimine (MW = 600) with 24 ethoxylate groups per —NH and 16 propoxylate groups per —NH.
[13]Huntsman, Salt Lake City, Utah, USA.
[14]Novozymes A/S, Bagsvaerd, Denmark.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing an alkylbenzene and a detergent alcohol from a natural oil and kerosene comprising:
    a) providing a first feed stream comprising natural oil;
    b) deoxygenating said first feed stream to form a stream comprising bio-paraffins;
    c) removing volatile components and gases from said stream comprising bio-paraffins to form a purified bio-paraffin stream;
    d) fractionating said purified bio-paraffin stream into three fractions, wherein a first fraction comprises a lower boiling range, a second fraction comprises a middle boiling range, and a third fraction comprises a high boiling range wherein the first, second and third fractions are free from geologically derived carbon;
    e) providing a second stream comprising kerosene;
    f) hydrotreating said second stream;
    g) sieving said hydrotreated second stream to form a stream comprising kerosene-based paraffin;
    h) combining said first fraction of purified bio-paraffin with said kerosene-based paraffin;

i) dehydrogenating said combination of said first fraction of purified bio-paraffin and said kerosene-based paraffin to form a stream comprising olefins;
j) alkylating said stream comprising olefins with a third feed stream comprising benzene to form a stream comprising alkylbenzenes;
k) dehydrogenating said second fraction of purified bio-paraffin to form a stream comprising olefins and paraffins;
l) separating said olefins from said paraffins in said stream comprising olefins and paraffins to form an olefin stream;
m) hydroformylating said olefin stream to form a stream comprising detergent alcohols.

2. The method of claim 1, wherein said third fraction of purified bio-paraffin is sulfoxidized to form a stream comprising paraffin sulfonate.

3. The method of claim 1, wherein said purified paraffin stream has greater than about 90% purity, wherein said purified paraffin stream comprises less than about 5% branched paraffins, less than about 3% olefins and cyclic compounds, and less than about 2% alcohols, esters, aldehydes, and fatty acids.

4. The method of claim 1, wherein said purified bio-paraffin stream comprises paraffins ranging in chain length from C10 to C18.

5. The method of claim 1, wherein said second feed stream comprises renewable benzene.

6. The method of claim 1, wherein said natural oil is selected from the group consisting of coconut oil, palm kernel oil, palm oil, and mixtures thereof.

7. The method of claim 1, wherein said alkylbenzenes are sulfonated.

8. The method of claim 1, wherein said detergent alcohols are sulfated.

* * * * *